(12) United States Patent
Keimel

(10) Patent No.: US 9,592,398 B2
(45) Date of Patent: Mar. 14, 2017

(54) LEADLESS IMPLANTABLE MEDICAL DEVICE WITH OSMOTIC PUMP

(75) Inventor: John G. Keimel, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 448 days.

(21) Appl. No.: 13/106,664

(22) Filed: May 12, 2011

(65) Prior Publication Data

US 2012/0290025 A1 Nov. 15, 2012

(51) Int. Cl.

| A61N 1/375 | (2006.01) |
|---|---|
| A61M 31/00 | (2006.01) |
| A61N 1/05 | (2006.01) |
| A61N 1/37 | (2006.01) |
| A61B 5/00 | (2006.01) |
| A61N 1/372 | (2006.01) |
| A61B 5/0245 | (2006.01) |

(52) U.S. Cl.
CPC ......... *A61N 1/3756* (2013.01); *A61M 31/002* (2013.01); *A61N 1/0568* (2013.01); *A61N 1/0575* (2013.01); *A61N 1/3712* (2013.01); *A61B 5/0006* (2013.01); *A61B 5/0245* (2013.01); *A61B 5/686* (2013.01); *A61N 1/37247* (2013.01); *A61N 1/37282* (2013.01)

(58) Field of Classification Search
CPC .. A61N 1/371; A61N 1/0575; A61N 1/03756; A61N 1/0568; A61N 1/3712; A61N 1/37247; A61N 1/37282; A61M 31/002; A61B 5/0006; A61B 5/0245; A61B 5/686
USPC ....................................................... 607/2, 3
See application file for complete search history.

(56) References Cited

U.S. PATENT DOCUMENTS

| 4,671,285 A | 6/1987 | Walker |
| 4,711,251 A | 12/1987 | Stokes |
| 4,819,662 A | 4/1989 | Heil, Jr. et al. |
| 4,966,144 A | 10/1990 | Rochkind et al. |
| 5,265,608 A | 11/1993 | Lee et al. |
| 5,328,470 A | 7/1994 | Nabel et al. |

(Continued)

FOREIGN PATENT DOCUMENTS

| WO | WO 99/36563 | 7/1999 |
| WO | WO 01/68814 A2 | 9/2001 |

(Continued)

OTHER PUBLICATIONS

Denison et al., "A 2 µW 100 nV/rtHz Chopper-Stabilized Instrumentation Amplifier for Chronic Measurement of Neural Field Potentials," IEEE Journal of Solid-State.Circuits, vol. 42, No. 12 pp. 2934-2945, Dec. 2007.

(Continued)

*Primary Examiner* — Michael Kahelin
*Assistant Examiner* — Minh Duc Pham

(57) ABSTRACT

Techniques for delivering genetic material to a target tissue site of a patient via a leadless implantable medical device that includes a pump and a stimulation energy delivery element are described. In some examples, delivery of genetic material to the target tissue site causes transgene expression of tissue at the target tissue site, which may result in generation of new cells or modified properties of existing cells of the target tissue site, facilitating more effective and efficient treatment of a disorder of the patient.

17 Claims, 11 Drawing Sheets

(56) References Cited

U.S. PATENT DOCUMENTS

| | | | |
|---|---|---|---|
| 5,409,482 | A | 4/1995 | Diamantopoulos |
| 5,702,384 | A | 12/1997 | Umeyama et al. |
| 5,797,870 | A | 8/1998 | March et al. |
| 5,872,879 | A | 2/1999 | Hamm |
| 5,902,326 | A | 5/1999 | Lessar et al. |
| 6,151,525 | A | 11/2000 | Soykan et al. |
| 6,238,429 | B1 | 5/2001 | Markowitz et al. |
| 6,385,491 | B1 | 5/2002 | Lindemans et al. |
| 6,494,900 | B1 | 12/2002 | Salansky et al. |
| 6,565,777 | B2 | 5/2003 | Farrar et al. |
| 6,567,705 | B1 | 5/2003 | Stokes et al. |
| 6,749,617 | B1 | 6/2004 | Palasis et al. |
| 6,775,574 | B1 * | 8/2004 | Soykan .................. A61N 1/326 607/3 |
| 6,832,115 | B2 | 12/2004 | Borkan |
| 6,921,413 | B2 | 7/2005 | Mahadevan-Jansen et al. |
| 6,931,286 | B2 | 8/2005 | Sigg et al. |
| 7,190,993 | B2 | 3/2007 | Sharma et al. |
| 7,280,870 | B2 | 10/2007 | Nurmikko et al. |
| 7,288,108 | B2 | 10/2007 | DiMauro et al. |
| 7,349,618 | B2 | 3/2008 | Nielsen et al. |
| 7,736,301 | B1 | 6/2010 | Webler et al. |
| 2002/0007199 | A1 * | 1/2002 | Schaldach .......... A61N 1/36514 607/62 |
| 2002/0012914 | A1 | 1/2002 | Bureau et al. |
| 2002/0061589 | A1 | 5/2002 | King et al. |
| 2003/0050259 | A1 | 3/2003 | Blatt et al. |
| 2003/0073238 | A1 | 4/2003 | Dzekunov et al. |
| 2003/0191500 | A1 * | 10/2003 | Stokes ................... A61M 37/00 607/3 |
| 2004/0158289 | A1 | 8/2004 | Girouard et al. |
| 2005/0059999 | A1 | 3/2005 | Mongeon et al. |
| 2005/0070987 | A1 | 3/2005 | Erickson |
| 2005/0119704 | A1 | 6/2005 | Peters et al. |
| 2005/0119712 | A1 | 6/2005 | Shafer |
| 2006/0015146 | A1 * | 1/2006 | Girouard ................ A61N 1/306 607/3 |
| 2007/0053996 | A1 | 3/2007 | Boyden et al. |
| 2007/0054319 | A1 | 3/2007 | Boyden et al. |
| 2007/0066997 | A1 * | 3/2007 | He ......................... A61N 1/372 607/3 |
| 2007/0225674 | A1 | 9/2007 | Molnar et al. |
| 2007/0261127 | A1 | 11/2007 | Boyden et al. |
| 2008/0077190 | A1 | 3/2008 | Kane et al. |
| 2008/0085265 | A1 | 4/2008 | Schneider et al. |
| 2008/0102119 | A1 | 5/2008 | Grovender et al. |
| 2008/0103537 | A1 * | 5/2008 | Sigg ........................ A61N 1/362 607/3 |
| 2008/0180278 | A1 | 7/2008 | Denison |
| 2008/0269841 | A1 | 10/2008 | Grevious et al. |
| 2009/0054954 | A1 | 2/2009 | Foley et al. |
| 2009/0082691 | A1 | 3/2009 | Denison et al. |
| 2009/0088680 | A1 | 4/2009 | Aravanis et al. |
| 2009/0093403 | A1 | 4/2009 | Zhang et al. |
| 2009/0099038 | A1 | 4/2009 | Deisseroth et al. |
| 2009/0099627 | A1 | 4/2009 | Molnar et al. |
| 2009/0118800 | A1 | 5/2009 | Deisseroth et al. |
| 2009/0192558 | A1 * | 7/2009 | Whitehurst .......... A61N 1/0551 607/3 |
| 2009/0281528 | A1 | 11/2009 | Grovender et al. |
| 2010/0023071 | A1 * | 1/2010 | Yomtov ............... A61K 9/0097 607/3 |
| 2010/0099965 | A1 | 4/2010 | Jacobson et al. |
| 2010/0161017 | A1 | 6/2010 | Choi et al. |
| 2010/0174329 | A1 * | 7/2010 | Dadd ................. A61N 1/36032 607/3 |

FOREIGN PATENT DOCUMENTS

| | | |
|---|---|---|
| WO | WO 02/19966 A2 | 3/2002 |
| WO | WO 02/24248 A1 | 3/2002 |
| WO | WO 2006/055582 A2 | 5/2006 |
| WO | WO 2008/061135 A2 | 5/2008 |

OTHER PUBLICATIONS

Berndt et al., "Bi-stable neural state switches," *Nature Neuroscience*, vol. 12, Dec. 2008, 6 pages.

Han et al., "Multiple-Color Optical Activation, Silencing, and Desynchronization of Neural Activity, with Single-Spike Temporal Resolution," PLoS One, 2(3):e299, http://www.plosone.org/article/info:doi/10.1371/journal.pone.0000299, Mar. 2007.

Yan et al., "Cloning and Characterization of Human $\beta,\beta$-Carotene-15,15'-Dioxygenase That Is Highly Expressed in the Retinal Pigment Epithelium," Genomics 72 (2), pp. 193-202, 2001.

Dittgen et al., "Lentivirus-based genetic manipulations of cortical neurons and their optical and elctrophysiological monitoring in vivo," Proc. Natl. Acad. Sci. USA, vol. 101, No. 52, pp. 18206-18211, Dec. 28, 2004.

Nagel et al., "Channelrhodopsin-2, a directly light-gated cation-selective membrane channel," Proc. Natl. Acad. Sci. USA, vol. 100, No. 24, pp. 13940-13945, Nov. 25, 2003.

Huang et al., "Plasmonic Photothermal Therapy (PPTT) Using Gold Nanoparticles," Lasers Med Sci, 23, pp. 217-228, 2008.

Hollister, "Medtronic debuts tiny lead-less pacemaker at TEDMED 2010," posted Oct. 28, 2010, at http://www.engadget.com/2010/10/28/medtronic-debuts-tiny-lead-less-pacemaker-at-tedmed-2010/, 1 p.

Theeuwes et al., "Principles of the Design and Operation of Generic Osmotic Pumps for the Delivery of Semisolid or Liquid Drug Formulations," Annals of Biomedical Engineering, vol. 4, No. 4, Dec. 1976, 11 pp.

Qu et al., "Expression and Function of a Biological Pacemaker in Canine Heart," pp. 1106-1109, 2003, http://www.circulationaha.org.

Miake et al. "Bilogical packemaker created by gene transfer," Brief Communications Nature, vol. 419, pp. 132-133, Sep. 12, 2002. http://www.nature.com/nature.

Anchordoquy et al., "Maintenance of Transfection Rate and Physical Characterization of Lipid/DNA Complexes after Freeze-Drying and Rehydration," Archives of Biochemistry and Biophysics, vol. 348, No. 1, pp. 199-206, Dec. 1997.

Pakkanen et al., "Periadventitial *lacZ* gene transfer to pig carotid arteries using a biodegradable collagen collar or a wrap of collagen sheet with adenoviruses and plasmid-liposome complexes," The Journal of Gene Medicine 2, pp. 52-60, 2000.

U.S. Appl. No. 12/951,766, by Timothy J. Denison, filed Nov. 22, 2010.

U.S. Appl. No. 12/951,852, by Timothy J. Denison, filed Nov. 22, 2010.

U.S. Appl. No. 12/907,481, by William J. Hintz, filed Oct. 19, 2010.

\* cited by examiner

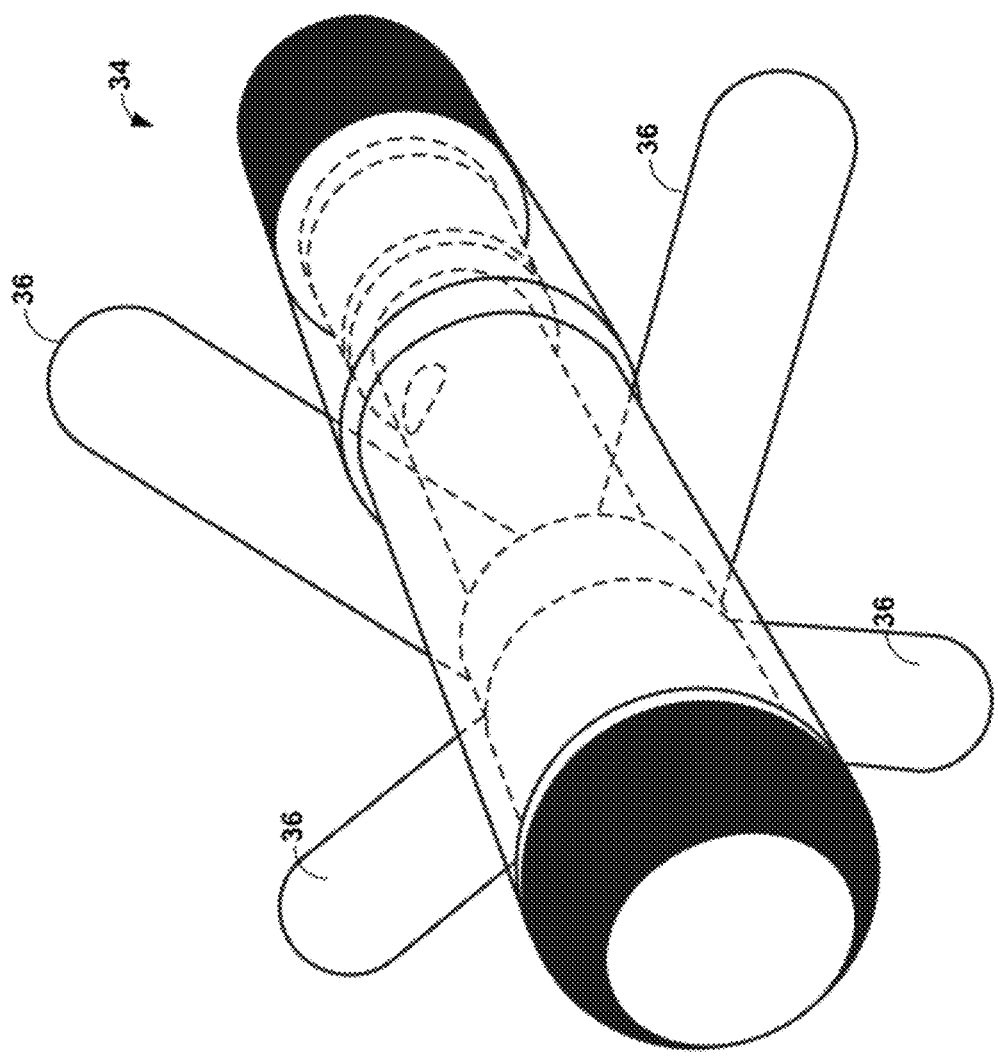

LEADLESS IMPLANTABLE MEDICAL DEVICE WITH OSMOTIC PUMP

TECHNICAL FIELD

The invention relates to medical devices and, more particularly, to delivery of genetic material and stimulation to a target tissue site via medical devices.

BACKGROUND

Implanted medical devices, such as implanted cardiac pacemakers, generally rely on a battery to provide energy for delivery of therapeutic stimulation, such as cardiac pacing. In general, when a primary battery of an implanted medical device is exhausted, the medical device must be explanted, and a new medical device implanted in its place. In some examples, medical devices have a rechargeable (secondary) battery which requires the patient to periodically recharge the battery in order for the unit to continue to function. Consequently, in order to prolong the useful life of medical devices or the time between required battery recharging, it is desirable to deliver stimulation with the lowest magnitude, e.g., electrical stimulation at the lowest current and voltage amplitude, that provides adequate therapeutic benefit. For example, it is generally desirable to deliver pacing pulses at the lowest energy that is still adequate to capture the heart.

Some implantable stimulators have used nucleonic batteries, but such stimulators are currently no longer commercially available. Other implantable stimulators have been described that generate power based on the body or heart movement, hemodynamic pressure changes, or other factors. For these devices, the size of the power generator within the implantable stimulator must be adequate for the energy consumed by the device. Therefore, even for these self-powered devices, there is an advantage to minimizing the energy used for tissue stimulation, e.g., reducing the size of the power generator and other components.

Currently available implantable cardiac pacemaker systems require the power source to be implanted distant from the heart because its size limits it from being placed in or on the heart. A cardiac lead is therefore required for directing stimulation energy from the electronics and battery package to the heart tissue. The movement of the heart and normal activity of the individual may, in some examples, subject the lead to forces that may result in lead related conditions, e.g., lead breakage or dislodgement of the electrodes from the heart tissue. Thus, in some examples, the size of the pacemaker battery also affects the efficacy of an implantable cardiac pacing system by imposing a need for a cardiac lead.

Existing techniques for prolonging the life of pacemaker power sources or decreasing the size of the power source include use of manual programming, e.g., reduction, of stimulation parameters to the minimum safe output for capture, or the use of automatic capture threshold detection algorithms to maintain pacing pulse energy at the lowest level necessary for capture. Other existing techniques are directed toward reducing the pacing pulse energy level required to capture the heart. Such techniques include use of electrode designs that concentrate current in a small area in order to increase the efficiency of stimulation.

Other electrodes incorporate a means of drug elution, such as steroids, e.g., as disclosed in U.S. Pat. No. 4,711,251 to Stokes entitled "BODY IMPLANTABLE LEAD," which issued on Dec. 8, 1987, and is herein incorporated by reference in its entirety. With these drug eluting leads, small molecule steroids, such as dexamethasone, may diffuse from the end of the lead and into the tissue adjacent to the stimulation electrode. This localized steroid delivery may reduce chronic tissue fibrotic encapsulation which may otherwise increase the required stimulation energy over time. Steroid eluting electrodes are currently commercially available, such as those used in active and passive fixation CapSure® cardiac lead models, made commercially available Medtronic, Inc of Minneapolis, Minn.

SUMMARY

In general, the disclosure is directed to delivering genetic material to a target tissue site of a patient via a leadless implantable medical device (IMD) that includes a pump and one or more stimulation energy delivery elements positioned on or within the leadless IMD. In some examples, delivery of genetic material to the target tissue site causes transgene expression at the target tissue site. Transgene expression within cells at the target tissue site may result in modified properties of the cells at the target tissue site (e.g., reduced stimulation threshold requirements or expression of biological pacemaker cell characteristics), which may facilitate more efficient treatment of a disorder of the patient using the leadless IMD.

In one example, the disclosure is directed to a leadless implantable medical device that includes a housing defining an outer surface and comprising an outlet, a stimulation energy delivery element positioned on the outer surface of the housing, a stimulation module within the housing and coupled to the stimulation energy delivery element, and a pump positioned within the housing. The stimulation module is configured to deliver stimulation to a target tissue site of a patient adjacent to the outer surface of the housing via the stimulation energy delivery element and the pump is configured to store genetic material and to deliver the genetic material to the target tissue site via the outlet.

In another example, the disclosure is directed to a method that includes delivering genetic material to a target tissue site of a patient via a pump of a leadless implantable medical device. The leadless implantable medical device includes a housing defining an outer surface and comprising an outlet, a stimulation energy delivery element positioned on the outer surface of the housing, a stimulation module within the housing and coupled to the stimulation energy delivery element, where the stimulation module is configured to deliver stimulation to a target tissue site of a patient adjacent to the outer surface of the housing via the stimulation energy delivery element, a pump reservoir positioned within the housing, where the pump reservoir is configured to store genetic material, and the pump, where the pump delivers the genetic material to the target tissue site via the outlet.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIG. 3 is a schematic diagram illustrating an example leadless IMD that includes a plurality of fixation elements.

DETAILED DESCRIPTION

Figure 1:
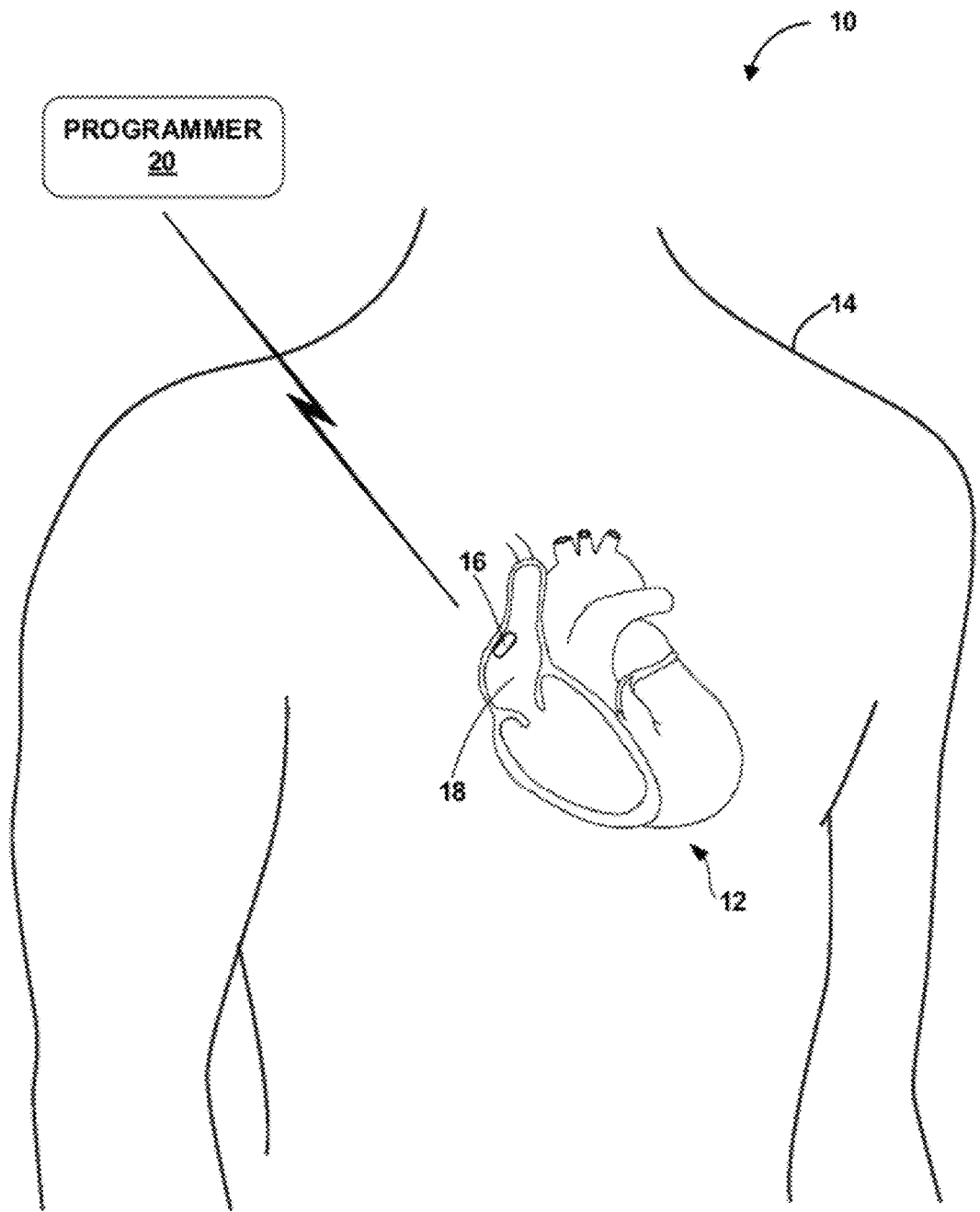
FIG. 1 is a conceptual diagram illustrating an example system that includes a leadless implantable medical device (IMD) for delivering genetic material to a target tissue site of a patient via a pump.

Some patient disorders may be treated via delivery of stimulation to a target tissue site within the patient. For example, an implantable medical device (IMD) may be implanted within the patient and positioned to deliver electrical stimulation to the target tissue site via a plurality of electrodes. In some examples, delivery of genetic material to the target tissue site may help to increase the efficiency of the stimulation delivered to the target tissue site.

Delivery of genetic material to the target tissue site may induce transgene expression within cells of the target tissue site to modify the electrode-tissue interface. In some examples, the transgene expression may result in modification of the cellular transmembrane ionic current of the cells at the target tissue site. For example, if the patient suffers from a cardiac disorder, the cellular transgene expression may cause these cells to act as a new biological pacemaker cells within the heart of the patient. The newly generated biological pacemaker cells may be capable of inducing a normal cardiac rhythm autonomously (e.g., without the help of the IMD). Consequently, the patient may require less frequent electrical stimulation or no electrical stimulation to treat the disorder of the patient after full expression of the genes, which may result in more efficient electrical stimulation therapy. In these examples, delivery of electrical stimulation may be required only between implantation of the leadless IMD and the time at which the genes are being adequately expressed, or as back-up if the newly generated pacemaker cells lose effectiveness over time.

In other examples, the transgene expression may result in modifications to properties of the cells of the target tissue site, such as modifications of the stimulation threshold required to activate one or more cells of the target tissue site via the electrodes of the IMD to efficiently treat the disorder of the patient. In examples in which a stimulation threshold of the cells at the target tissue site is reduced, the patient may require less intense electrical stimulation, which may facilitate more efficient electrical stimulation therapy and longer battery life of the IMD.

Sequences of genetic material, e.g., chains of deoxyribonucleic acid (DNA) or ribonucleic acid (RNA), and particles containing genetic material may, in some examples, have a physical molecular size which results in a low diffusion coefficient. As a result, genetic material may not diffuse far from the injection site. In some examples, intraparenchymal injection of genetic material may result in flow of the fluid vehicle containing the genetic material and thereby allow convection of genetic material.

The concept of using a back pressure higher than that of the tissue in order to cause flow of the fluid containing the genetic material is termed convection enhanced delivery (CED), which has been described in U.S. Pat. No. 5,720,720 to Laske et al., entitled "CONVECTION-ENHANCED DRUG DELIVERY," which issued on Feb. 24, 1998 and is incorporated herein by reference in its entirety. Convection of the genetic material may result in a greater volume of distribution than that possible with diffusion alone, but the volume of distribution may be limited by the size of the particle and the affinity of the particles to cells within tissue. Thus, the volume of cells sufficiently transduced by an injection may be limited to a small volume surrounding the injection site. For example, without inducing damage to the tissue during the injection, the volume of distribution, e.g., resulting from CED injection of adeno-associated viral vectors (AAVs) carrying genetic material, may be limited to less than one cubic centimeter.

The genetic modification of tissue to reduce the pacing threshold or to express light-responsive ion channels, for example, may be limited to this volume. The volume of tissue stimulated directly by an electrode or light-emitting element is also limited to the tissue volume immediately surrounding and near the electrode or light-emitting element. For example, with typical cardiac pacemaker electrodes and stimulation parameters, only the cells within approximately two millimeters from the pacing electrode may be depolarized. If the volume of transfected tissue is co-located with the volume of tissue near the stimulation output source, the pacemaker system may benefit more from the reduced pacing threshold resulting from genetic modification at the target tissue site.

Ultimately, it is desirable to cure a patient's condition for his or her lifetime. The present disclosure describes examples in which delivery of cell-modifying genetic material to the target tissue site is intended to reduce the cellular stimulation threshold at the target tissue site, and also facilitate co-location of the stimulation output source and the target tissue site. As a result, in some examples, the device battery size or power supply may be reduced, or the life of the power source may be increased. Some examples herein describe delivery of cell-modifying genetic material intended to create a biological replacement for failed tissue (e.g., the sino-atrial node) and to synergistically provide the added safety and reliability of a stand-by implantable leadless pacemaker.

The examples herein are described with respect to delivering genetic material and stimulation via the leadless IMD to a heart of a patient to treat a cardiac disorder of the patient. However, in other examples, genetic material and stimulation may be delivered to other target tissue sites of the patient to treat another type of disorder of the patient.

FIG. 1 is a conceptual diagram illustrating an example therapy system 10 for treating a cardiac disorder of patient 14. System 10 includes leadless IMD 16 and external programmer 20, which may communicate with one another, e.g., via wireless telemetry. In the example illustrated in FIG. 1, leadless IMD 16 is implanted within right atrium 18 of heart 12 of patient 14, proximate to the sinoatrial (SA) node of patient 14. In other examples, leadless IMD 16 may be implanted proximate to another portion of heart 12 of patient 14.

Leadless IMD 16 may provide one or more advantages. For example, a leadless IMD may eliminate the need for an implantable lead, and may also require a smaller power source such that a stimulator of the IMD may be positioned directly at the target tissue site. Example leadless pacemakers and neurological stimulators are described in, for example, U.S. Pat. No. 3,943,936 which issued to Rasor et al. on Mar. 16, 1976, entitled "SELF POWERED PACERS AND STIMULATORS," and which is incorporated herein by reference in its entirety.

Although the example systems and techniques are primarily described herein with respect to delivering electrical stimulation to the target tissue site via a plurality of housing electrodes, in other examples, the systems and techniques may be applicable to other types of stimulation of the target tissue site. In some examples, such as described below with respect to FIGS. 4B and 5B, IMD 16 may deliver optical stimulation to the target tissue site of patient 14 via an optical stimulation energy delivery element (e.g., a light source), and may deliver genetic material to modify properties of cells at the target tissue site to improve the efficiency of the optical stimulation therapy. For example, as with electrical stimulation therapy, in some examples, the genetic material may function to decrease an optical stimulation threshold requirement for activation of tissue at the target tissue site, or induce cells at the target tissue site to exhibit biological pacemaker cell properties such that less optical stimulation energy is required for treatment of the patient disorder.

In addition, although the example systems and techniques are primarily described herein with respect to delivering electrical stimulation to a target tissue site within or on heart 12 of patient 14 to treat a cardiac disorder, in other examples, the systems and techniques may be applicable to stimulation of other types of target tissue sites. For example, the systems and techniques may be utilized to excite cells that are found in skeletal, smooth muscle, pancreatic, and neural tissue. In some examples, the systems and techniques described herein are applicable to deep brain stimulation for the treatment of Parkinson's disease or stimulation of the spinal cord or peripheral nerves for the treatment of pain. In some examples, the systems and techniques described herein may be used to deliver stimulation and genetic material to target tissue sites within the brain or spinal cord of patient 14, gastrointestinal tissue to support gastrointestinal therapy such as therapy to address obesity, motility disorders (e.g., gastroparesis), dyspepsia, or other therapies, pelvic floor tissue (e.g., sacral or pudendal nerve tissue) to support pelvic floor therapy such as pain therapy, urinary or fecal incontinence therapy, sexual dysfunction, or other therapies, or cranial tissue to support cranial nerve therapy such as therapy to relieve occipital neuralgia, trigeminal neuralgia, facial pain, migraine headaches, other target nerves of patient 14, and the like.

As discussed in more detail with respect to FIGS. 2-5B, leadless IMD 16 includes a housing and a stimulation energy delivery element positioned on the housing or within the housing and controlled by a stimulation module to deliver stimulation to a target tissue site. In addition, leadless IMD 16 includes a pump reservoir within the housing that stores genetic material and a pump within the housing that delivers the genetic material to the target tissue site. As discussed above, delivery of genetic material to the target tissue site can improve properties of cells of the target tissue site to increase the efficiency of treatment of the disorder of patient 14. The genetic material delivered to the target tissue site via the pump of IMD 16 may take any suitable form. In some examples, the genetic material may be delivered via a viral vector, such as an adenoviral or adeno-associated viral vector. Additionally or alternatively, the genetic material may be delivered via a liposomal vector or as a plasmid deoxyribonucleic acid (DNA). The delivered genetic material causes transgene expression by the tissue located at the target tissue site, which may modify properties of the tissue at the target tissue site.

As previously mentioned, in some examples, genetic material delivered via IMD 16 may modify the properties of cells at the target tissue site such that the cells periodically depolarize without stimulation by the IMD 16. For example, some patients may suffer from cardiac disorders that result from abnormal function of one of the pacemaker nodes of the heart, e.g., the sinoatrial (SA) node or the atrioventricular (AV) node, and particular types of genetic material may be selected that induce transgene expression to modify cells so as to become biological pacemaker cells to improve or restore functionality. However, adequate expression of the genes may not occur immediately upon delivery of the genetic material.

Thus, patient 14 may require delivery of stimulation to the region of heart 12 proximate the target tissue site, for a period of time. Such delivery of stimulation may maintain normal electrical activity of heart 12 until adequate expression of the genes occurs, and the generated biological pacemaker cells can function effectively without delivery of stimulation or with delivery of less intense stimulation. In addition, in some examples, the newly generated biological pacemaker cells may not have permanent efficacy, and the stimulation components of IMD 16, e.g., the stimulation module and stimulation energy delivery element, may provide back-up stimulation during periods of time in which the generated biological pacemaker cells do not maintain full efficacy.

In the example illustrated in FIG. 1, IMD 16 is positioned proximate to the SA node of heart 12 of patient 14. When functioning normally, the SA node of heart 12 is the pacemaker for heart 12 and generates action potentials that establish a normal rhythm of heart 12. However, when the SA node of patient 12 functions abnormally, patient 12 may require therapy and/or treatment to maintain a normal sinus rhythm of heart 12. For example, IMD 16 may deliver electrical stimulation to heart 12 to pace heart 12.

In the example illustrated in FIG. 1, IMD 16 is fully positioned within right atrium 18 of heart 12. Thus, both the stimulation components and the osmotic pump of IMD 16 are positioned within right atrium 18 to deliver genetic material and electrical stimulation to the target tissue site. In some examples, such a configuration facilitates generation of new biological pacemaker cells as a substitute for a non-functional or minimally-functional SA node, while maintaining normal sinus rhythm of heart 12. For example, the genetic material delivered via the osmotic pump of IMD 16 may induce transgene expression within tissue of the right atrium 18, and the electrical stimulation components of IMD 16 may maintain normal sinus rhythm of heart 12 until adequate expression of the genes is achieved and new biological pacemaker cells have been generated.

The genetic material may include any agents configured to cause transgene expression that results in transformation of cells to biological pacemaker cells. For example, the genetic material may include one or more nucleic acids that encode particular genes, such as MiRP1 and one or more HCN channels. Examples of one or more types of suitable genetic materials are described in U.S. Patent Application Publication No. 2002/0187948 by Rosen et al., entitled "IMPLANTATION OF BIOLOGICAL PACEMAKER THAT IS MOLECULARLY DETERMINED," which was published on Dec. 12, 2002 and is incorporated herein by reference in its entirety. As another example, the genetic material may be selected to control the regulation of the expression of particular ion channels, e.g., K.sup.+ channels, as described in U.S. Pat. No. 6,214,620 which issued to Johns et al. on Apr. 10, 2011, entitled "INDUCIBLE GENETIC SUPRESSION OF CELLULAR EXCITABILITY" and incorporated herein by reference in its entirety. As another example, the genetic material may be selected to modify inwardly rectifying K.sup.+ channels (I.sub.K1) in quiescent ventricular cells, as described in PCT Application No. WO 2002/02098286 by Eduardo, entitled "BIOLOGICAL PACEMAKER," which was published on Nov. 7, 2002 and is incorporated herein by reference in its entirety.

Additionally or alternatively, genetic material delivered via IMD 16 may be selected to modify properties of existing tissue at the target tissue site, e.g., to lower the stimulation energy requirements for capture. For example, particular types of genetic material may be effective for causing transgene expression that reduces a stimulation threshold necessary to activate cells at the target tissue site, e.g., to induce depolarization. As another example, particular types of genetic material may be effective for causing expression of anti-inflammatory or immunosuppressant agents, which can increase biocompatibility of IMD 16 with surrounding tissue and also reduce the stimulation energy necessary to activate cells at the target tissue site. In these examples, transgene expression resulting from delivery of genetic material to the target tissue site via the osmotic pump of IMD 16 may increase the efficiency of the electrical stimulation delivered to the target tissue site via the stimulation components of IMD 16.

In some examples, the genetic material may cause increased expression of ion channels, or the like, within tissue of the target tissue site resulting in a decrease of the stimulation threshold of these cells. A decrease in stimulation threshold may result in capture of heart 12 with stimulation defined by a reduced intensity, e.g., amplitude. As another example, the genetic material may induce expression of metalloproteinases, or anti-inflammatory or immunosuppressant agents, which affect extracellular matrix physiology and/or remodeling and may reduce fibrous growth and/or inflammation at the target tissue site. An exemplary anti-inflammatory agent that may be expressed is IκB, or other anti-inflammatory mediators of the NF-κB cascade. Reduced fibrous growth and/or inflammation at the stimulation site may facilitate reduced pacing pulse amplitude necessary to capture heart 12.

In addition to leadless IMD 16, system 10 may include external programmer 20, which communicates with leadless IMD 16. In some examples, programmer 20 comprises a handheld computing device, computer workstation, or networked computing device. Programmer 20 includes a user interface that presents information to and receives input from a user. It should be noted that the user may also interact with programmer 20 remotely via a networked computing device.

A user, such as a physician, technician, surgeon, electrophysiologist, other clinician, or patient, interacts with programmer 20 to communicate with leadless IMD 16. For example, external programming capabilities may allow options for manually conducting stimulation threshold tests and reprogramming the stimulation parameters in order to minimize the necessary stimulation energy. In addition, the user may interact with programmer 20 to retrieve physiological or diagnostic information from leadless IMD 16. A user may also interact with programmer 20 to program leadless IMD 16, e.g., select values for operational parameters of leadless IMD 16. For example, the user may use programmer 20 to retrieve information from leadless IMD 16 regarding the rhythm of heart 12, trends therein over time, or arrhythmic episodes.

In some examples, the user may use programmer 20 to retrieve information from leadless IMD 16 regarding other sensed physiological parameters of patient 14 or information derived from sensed physiological parameters, such as intracardiac or intravascular pressure, activity, posture, respiration, tissue perfusion, heart sounds, or a cardiac electrogram (EGM), e.g., to assess the status of the genetically modified tissue. In some examples, the user may interact with programmer 20 to program, e.g., select parameters and values for, therapies and sensing performed by leadless IMD 16.

IMD 16 and programmer 20 may communicate via wireless communication using any techniques known in the art. Examples of communication techniques may include, for example, low frequency or radiofrequency (RF) telemetry, but other techniques are also contemplated.

Figure 2:
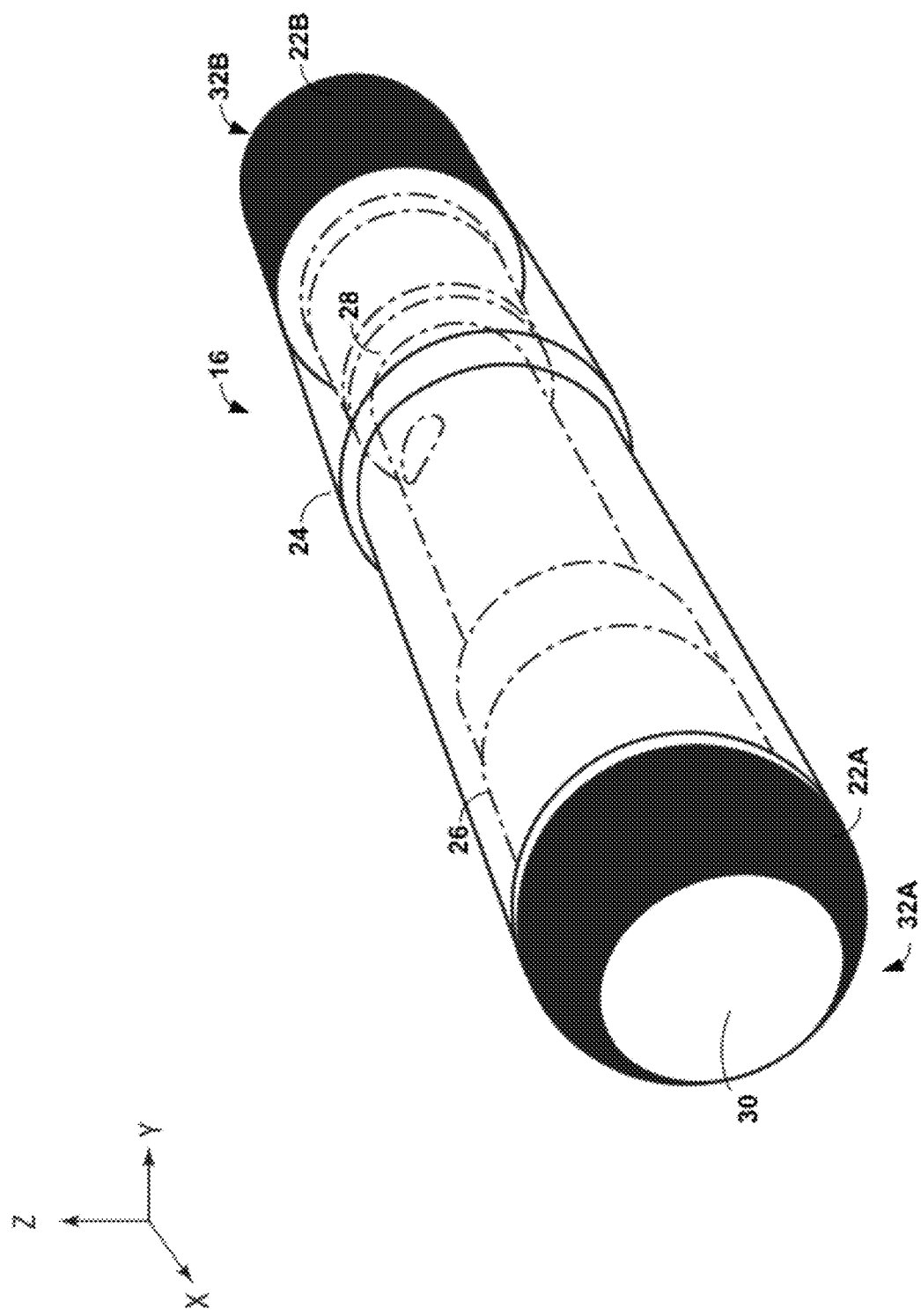
FIG. 2 is a schematic diagram illustrating an example leadless IMD that includes an osmotic pump and a plurality of stimulation electrodes.

FIG. 2 is a schematic perspective view of leadless IMD 16. As illustrated in FIG. 2, IMD 16 includes two housing electrodes 22A and 22B (collectively referred to as "housing electrodes 22") positioned on housing 24 of IMD 16, osmotic pump 26, and stimulation module 28. Osmotic pump 26 is configured to deliver genetic material to the target tissue site within patient 12 via outlet 30, and stimulation module 28 is configured to deliver electrical stimulation to the target tissue site via housing electrodes 22.

As illustrated in FIG. 2, leadless IMD 16 is formed in the shape of a cylinder extending in an x-axis direction (orthogonal x-y-z axes are shown for ease of description only) between ends 32A and 32B (collectively referred to as "ends 32"). In the example illustrated in FIG. 2, ends 32 are rounded. In some examples, rounded ends 32 may increase biocompatibility of IMD 16 with surrounding tissue upon implantation by eliminating sharp edges that may disrupt cardiac tissue at the target tissue site within heart 12. In other examples, leadless IMD 16 may be formed in another suitable shape, e.g., a circular, rectangular, or elliptical shape. As illustrated in FIG. 3, in some examples, a leadless IMD may additionally include a fixation element 36 coupled to the housing of the IMD to secure the IMD proximate to the target tissue site within patient 12. The fixation elements 36 can take the form of tines, as illustrated in FIG. 3, or utilize other fixation techniques known in the art, such as a helical coils, barbs, or combinations of these fixation elements.

In some examples, leadless IMD 16 may have relatively small dimensions. For example, the IMD 16 may have a length between approximately one and approximately three centimeters and a diameter between approximately one and approximately four millimeters. In some examples, implantation of IMD 16 may require a less invasive procedure if IMD 16 has relatively small dimensions, in comparison to implantation of an IMD that has larger dimensions and/or additional components, e.g., a larger pectoral or abdominal IMD coupled to a medical lead or catheter. In addition, osmotic pump 26 and housing electrodes 22 of IMD 16 may deliver genetic material and electrical stimulation, respectively, to substantially the same target tissue within patient 12. That is, the portion of tissue to which osmotic pump 26 delivers genetic material and the portion of tissue to which housing electrodes 22 deliver electrical stimulation may be substantially aligned because IMD 16 directs the stimulation field to the same volume of tissue in which the genetic material is delivered (e.g., the volume of tissue transfected by the genetic material).

As illustrated in FIG. 2, IMD 16 includes housing 24, within which are housed osmotic pump 26 and stimulation module 28. Housing 24 defines an outer surface, and IMD 16 includes two housing electrodes 22A and 22B, mechanically coupled to the outer surface of housing 24 and electrically coupled to stimulation module 28 within housing 24. Housing 24 may have any suitable configuration. In some examples, housing 24 or a portion of housing 24 may be hermetically-sealed to prevent fluid from coming into contact with stimulation module 28 and other components housed within housing 24. As discussed in further detail below with respect to FIG. 4, in some examples, a portion of housing 24 surrounding osmotic pump 26 may be formed from a semi-permeable material that allows fluid from surrounding tissue to enter osmotic pump 26 to induce delivery of the genetic material stored in osmotic pump 26 to the target tissue.

Housing electrodes 22 may be any type of electrode suitable for delivering electrical stimulation to tissue of patient 14. In some examples, housing electrodes 22 may also be capable of sensing one or more signals related to physiological parameters of the target tissue site. Electrodes 22 may be formed integrally with the outer surface of housing 24 or otherwise coupled to housing 24. In this manner, electrodes 22 may be referred to as housing electrodes. In some examples, housing electrodes 22 are defined by uninsulated portions of an outward facing portion of housing 24 of IMD 16. Other division between insulated and uninsulated portions of housing 24 may be employed to define a different number or configuration of housing electrodes. For example, in an alternative configuration, IMD 16 may include a single housing electrode that comprises substantially all of housing 24, and may be used in combination with an electrode formed by a fixation mechanism of IMD 16 (e.g., a tine element as illustrated in FIG. 3) for delivery of therapy.

In the example illustrated in FIG. 2, housing electrode 22A defines a space through which outlet 30 of osmotic pump 26 extends to deliver genetic material to the target tissue site. In this example, housing electrode 22B defines such a space because IMD 16 includes only one osmotic pump 26 positioned proximate to end 32A of IMD 16. In other examples, outlet 30 of osmotic pump 26 may extend directly through a portion of housing 24 instead of through one of housing electrodes 22 to deliver genetic material. In any case, the outlet of the pump is directed to substantially the same tissue affected by the stimulation field.

Osmotic pump 26 and stimulation module 28 are illustrated within housing 24 by hidden lines. In some examples, osmotic pump 26 and/or stimulation module 28 includes one or more separate enclosures or housings within housing 24 that compartmentalizes components of osmotic pump 26 and/or stimulation module 28 within housing 24.

FIG. 3 illustrates a schematic perspective view of another example leadless IMD 34. Leadless IMD 34 is substantially similar to leadless IMD 16 of FIGS. 1 and 2. In addition, as illustrated in FIG. 3, IMD 34 includes fixation elements 36 configured to secure IMD 34 within heart 12 proximate to the target tissue site.

In the example illustrated in FIG. 3, fixation elements 36 include a plurality of tines configured to anchor leadless IMD 34 to a wall of heart 12 of patient 14. Additionally or alternatively, fixation elements 36 may include other types of fixation mechanisms suitable for securing IMD 34 proximate to the target tissue site. For example, fixation elements 36 may include screws (active or in-active), e.g., helical structures that may be screwed into a wall of heart 12, or adhesive materials.

In some examples, fixation elements 36 may include a conductive portion that may be used as an electrode to deliver electrical stimulation to heart 12. For example, one or more of fixation elements 36 may include a conductive portion mechanically coupled to the tip of the fixation element and electrically coupled to stimulation module 28 within IMD 34. In this way, stimulation module 28 may control delivery of electrical stimulation through the conductive portion of the fixation element 36.

Figure 4A:
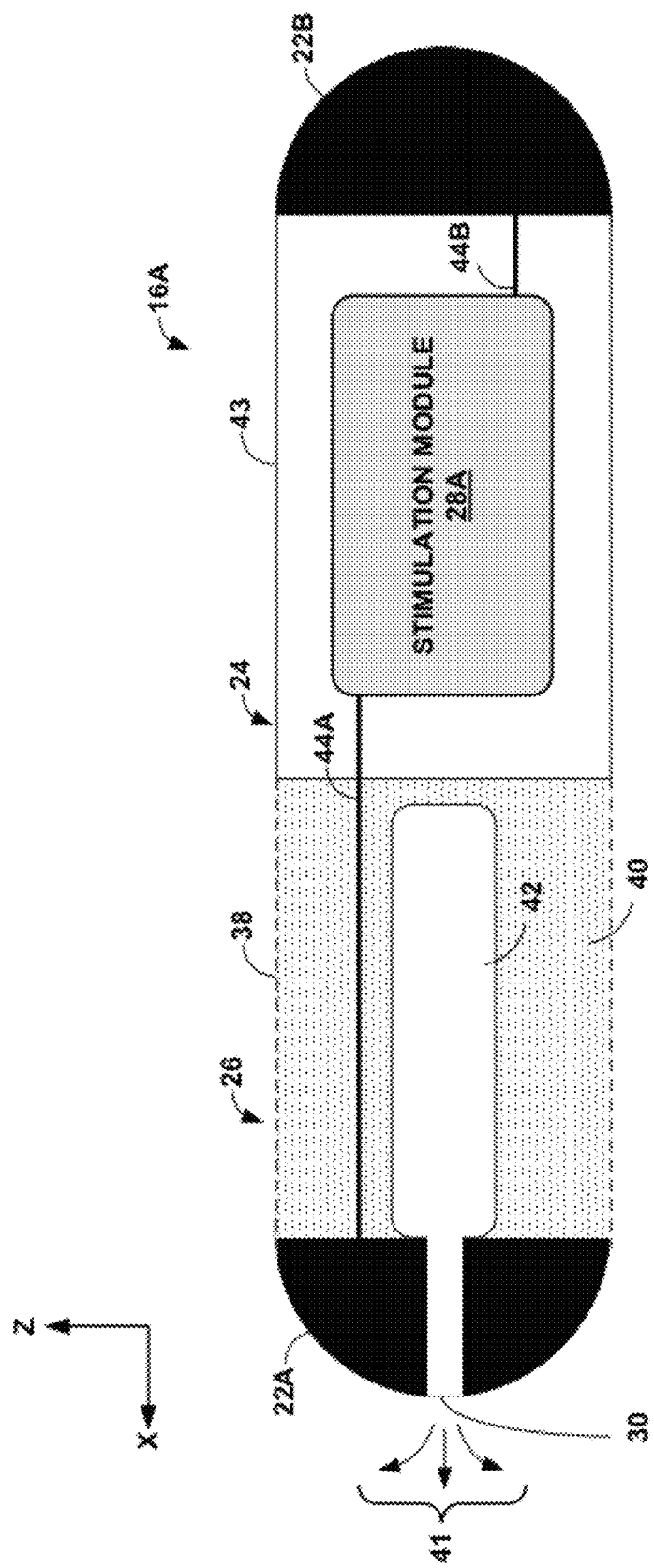
FIG. 4A is a cross-sectional diagram illustrating an example leadless IMD that includes an osmotic pump and a plurality of stimulation electrodes.

FIG. 4A is a schematic cross-sectional diagram illustrating leadless IMD 16A (FIGS. 1 and 2). The cross-section is taken in the x-z plane. (Orthogonal x-z axes are shown for ease of description only, and correspond to orthogonal x-y-z axes shown in FIG. 2.) As illustrated in FIG. 4A, IMD 16A includes osmotic pump 26, which includes semi-permeable membrane 38, osmotic material 40, and reservoir 42, and stimulation module 28A electrically coupled to housing electrodes 22 via conductors 44.

Figure 4B:
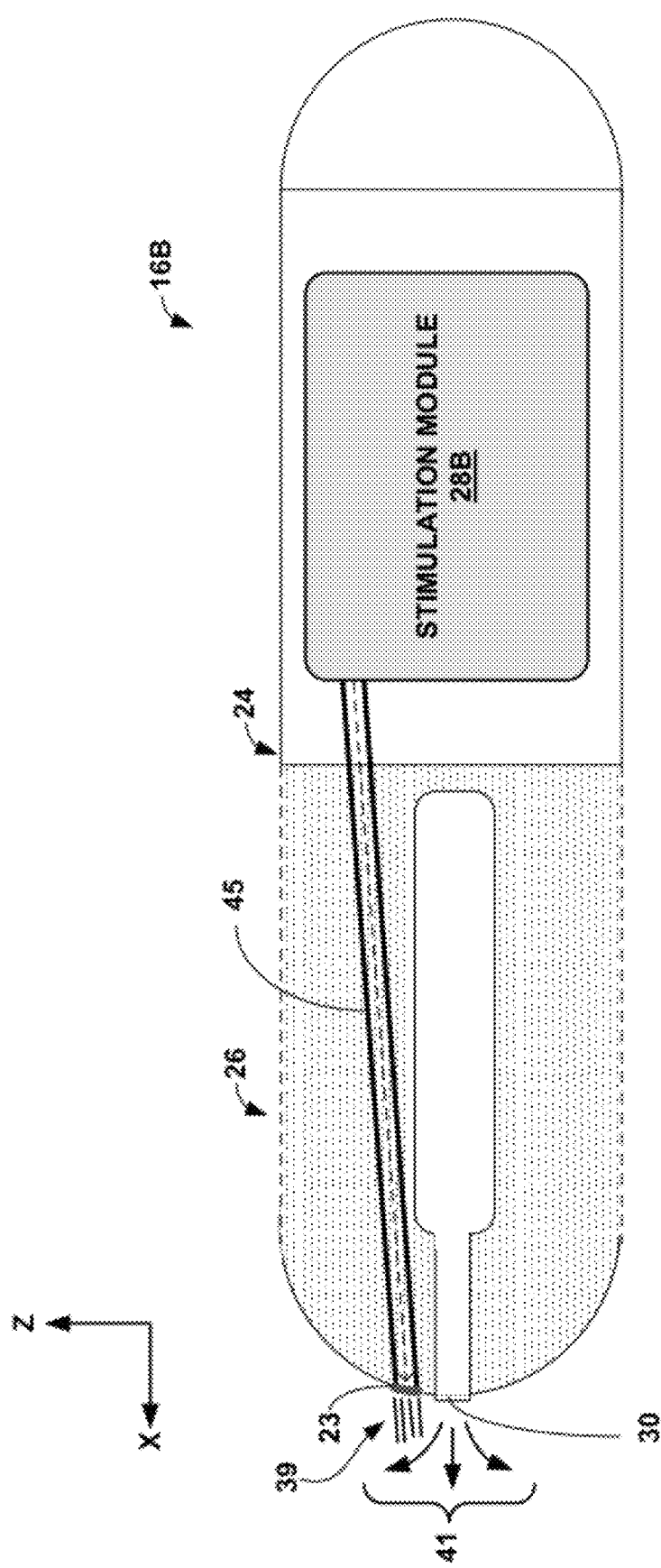
FIG. 4B is a cross-sectional diagram illustrating an example leadless IMD that includes an osmotic pump and an optical stimulation delivery element.

Osmosis may be defined as the movement of solvent molecules through a selectively-permeable membrane from a region of lower solute concentration into a region of higher solute concentration. Osmosis aims to equalize solute concentrations on both sides of the selectively-permeable membrane. In the examples briefly described herein, osmotic pump 26 uses osmosis to drive delivery of the genetic material stored within reservoir 42 out through outlet 30 to the target tissue site. As illustrated in FIGS. 4A and 4B, osmotic pump 26 includes reservoir 42 surrounded by and positioned within osmotic material 40, which is surrounded by semi-permeable membrane 38.

The operation and materials of an osmotic pump have been generally described by, for example, Theeuwes and Yum in "PRINCIPLES OF THE DESIGN AND OPERATION OF GENERIC OSMOTIC PUMPS FOR THE DELIVERY OF SEMISOLID OR LIQUID DRUG FORMULATIONS" (Annals of Biomedical Engineering, Vol. 4, No. 4, December 1976), which is incorporated by reference herein in its entirety.

Osmotic pump 26 includes semi-permeable membrane 38, which is selectively permeable to particular materials. In the examples described herein, semi-permeable membrane 38 is selectively permeable to water, which is a solvent, and may be formed from any suitable materials such that semi-permeable membrane 38 is selectively permeable to water.

Osmotic pump 26 also includes osmotic material 40, which has a relatively high concentration of a solute, such as a salt. Semi-permeable membrane 38 may be formed such that membrane 38 is permeable to water but impermeable to the solute of osmotic material 40. Thus, the solute of osmotic material 40 may not travel through semi-permeable membrane 38 and, consequently, remains within osmotic material 40.

Reservoir 42 of osmotic pump 26 is configured to store genetic material and deliver the genetic material to the target tissue site via outlet 30. As illustrated in FIG. 4A, reservoir 42 is surrounded by osmotic material 40 and defines a space into which the genetic material may be placed and stored. Outlet 30 is contiguous with the space in reservoir 42 in which the genetic material is stored and, thus, osmotic pump 26 may deliver the genetic material from reservoir 42 through outlet 30 to the target tissue site.

In examples where the reservoir 42 is filled with genetic material at the time of manufacture, the outlet 30 may include a semipermeable membrane or mesh that facilitates retention of the genetic material, such as by surface tension, within the reservoir 42 during periods of storage prior to implant, but does not prevent delivery of the genetic material when the osmotic pump is activated by insertion in body fluids of patient 14. The outlet 30 directs the flow of genetic material from within reservoir 42 into the target tissue, e.g., as illustrated by arrows 41 in FIG. 4A.

In the examples described herein, reservoir 42 is formed from a flexible impermeable material, such as an elastomer. Thus, the form or configuration of reservoir 42 may change if the form or configuration of osmotic material 40 surrounding reservoir 42 changes. For example, reservoir 42 may form a bag-like structure within osmotic material 40 such that, when osmotic material 40 expands or contracts, the material forming reservoir 42 correspondingly readjusts into the newly defined space within osmotic material 40.

Semi-permeable membrane 38, osmotic material 40, and reservoir 42 of osmotic pump 26 function cooperatively to deliver genetic material to the target tissue site via outlet 30. IMD 16 is implanted within tissue of patient 14, which has a high concentration of water. As discussed above, semi-permeable membrane 38 may be selectively permeable to water, and osmotic material 40 may have a high concentration of a solute, such as a salt. Thus, upon implantation of IMD 16 within patient 14 proximate to the target tissue site, water from the target tissue site may travel through semi-permeable membrane 38 into osmotic material 40 as a result of osmosis, because the concentration of solute within osmotic material 40 is higher than the concentration of solute at the target tissue site. Movement of water into osmotic material 40 may result in compression of reservoir 42, which, as previously discussed, may be formed from a flexible material, such as an elastomer. When reservoir 42 is compressed, the genetic material stored within reservoir 42 may be displaced and forced out of reservoir 42 through outlet 30, resulting in delivery of the genetic material to the surrounding tissue at the target tissue site.

In some examples, the rate of delivery of genetic material through outlet 30 to the target tissue site may be controlled by altering the permeability of the semi-permeable membrane 38, which consequently alters the rate at which osmotic material 40 compresses reservoir 42 and expels genetic material through outlet 30. In other examples, the rate of delivery of genetic material may be controlled by other means, such as by selecting an outlet 30 with particular properties that may set a particular rate of delivery. In some examples, the rate of delivery is selected such that little genetic material is lost during the implantation procedure and, upon implantation, the reservoir is emptied within, e.g., a few hours to a few days. Exemplary miniature osmotic pumps that may be incorporated into IMD 16 are Alzet® Osmotic Pumps made commercially available by DURECT Corporation of Cupertino, Calif.

As illustrated in FIGS. 4A and 4B, semi-permeable membrane 38 forms a portion of housing 24 of IMD 16. Housing 24 may include semi-permeable membrane 38 surrounding the portion of IMD 16 that includes osmotic pump 26 and a separate portion 43 of housing 24 surrounding stimulation module 28. In some examples, portion 43 of housing 24 may be hermetically sealed to prevent fluids and other biological materials from the target tissue site from contacting stimulation module 28, while semi-permeable membrane 38 is not hermetically sealed.

Figure 5A:
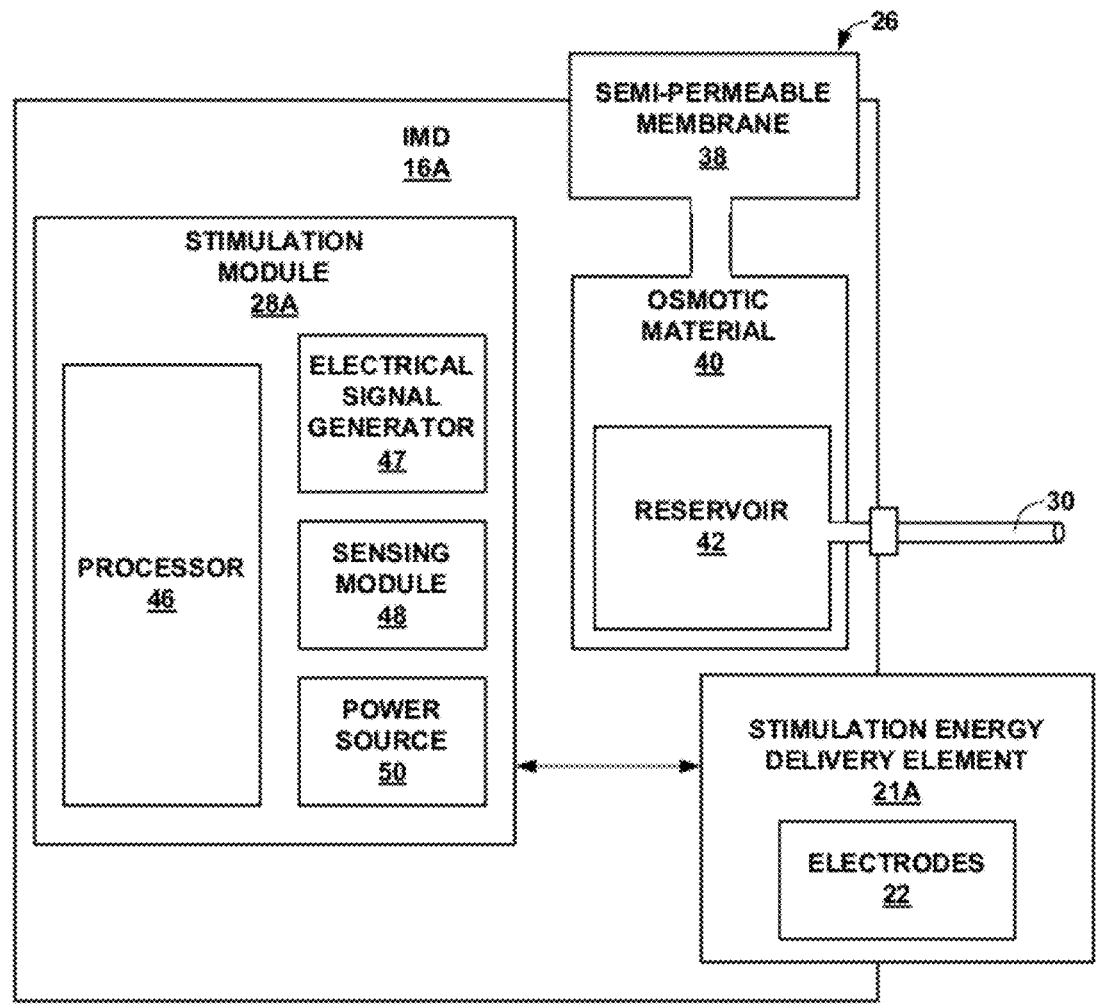
FIG. 5A is a functional block diagram illustrating an example configuration of a leadless IMD that includes an osmotic pump and a plurality of stimulation electrodes.

As illustrated in FIG. 4A, IMD 16 also includes stimulation module 28A positioned within housing 24. Stimulation module 28A may include any components necessary for delivering electrical stimulation to the target tissue site via housing electrodes 22. For example, as illustrated in FIG. 5A, stimulation module 28A may include a processor configured to control the delivery of electrical stimulation via housing electrodes 22 and a power source to provide operating power to IMD 16. In some examples, housing electrodes 22 also act as sensing electrodes such that housing electrodes 22 can sense signals associated with physiological parameters of tissue at the target tissue site, and stimulation module 28 may control sensing via the housing electrodes 22.

As illustrated in FIG. 4A, circuitry or other electronic components of stimulation module 28A may be electrically coupled to housing electrodes 22A and 22B via conductors 44A and 44B (collectively "conductors 44"), respectively. Conductors 44 may be formed from any suitable material and in any suitable configuration for effectively forming electrical connections between stimulation module 28A and housing electrodes 22 such that circuitry within stimulation module 28A can transmit and receive electrical signals to and from housing electrodes 22. For example, conductors 44 may be metal cables or bundles of metal cables.

In the example illustrated in FIG. 4, conductor 44A extends through osmotic material 40 to be coupled to housing electrode 22A. In some examples, the portion of conductor 44A within osmotic material 40 may include an insulated material surrounding a conducting material such that osmotic material 40 and the conducting material do not contact one another. Although FIG. 4A illustrates conductor 44A extending through the portion of IMD 16 surrounded by semi-permeable membrane 38, in other examples, conductor 44A may extend through a portion of IMD 16A enclosed by a hermetically-sealed section of housing 24.

FIG. 4B illustrates an IMD 16B, which is configured to deliver optical stimulation to the target tissue site of patient 14. In some examples, IMD 16B may be configured to deliver optical energy to the target tissue site such that the optical energy results in depolarization of cells at the target tissue site. For example, light pulses of the optical stimulation may be defined by sufficient parameters, e.g., amplitude, pulse width, pulse rate, etc., to cause depolarization in the cells. In some examples, power or energy of a light pulse delivered to the target tissue site may decrease with tissue penetration depth; consequently, in some examples, a leadless IMD 16B that positions the optical stimulation energy delivery element in close proximity with cells of the target tissue site modified by the genetic material may be desirable.

In some examples, the target tissue site may include cells with highly efficient cellular membrane ion channels that are responsive to low levels of optical stimulation. Delivery of genetic material to the target tissue site to genetically modify these cells may facilitate expression of these light-responsive ion channels such that the cells can be excited or activated by light. For example, Zhang et al. describes exemplary techniques for genetic modification of cells to be responsive to optical stimulation. Similarly, as another example, Berndt et al. describes genetic mutations to light responsive ion channels, e.g., mutations to channelrhodopsin-2, which may reduce the optical energy required for depolarization of cells which express these ion channels. Zhang et al. ("CHANNELRHODOPSIN-2 AND OPTICAL CONTROL OF EXCITABLE CELLS," *Nature Methods, Vol.* 3, No. 10, pp. 785-792, October 2006) and Berndt et al. ("BI-STABLE NEURAL STATE SWITCHES," *Nature Neuroscience, Vol.* 12, No. 2, pp. 229-234, February 2009 and "HIGH-EFFICIENCY CHANNELRHODOPSINS FOR FAST NEURONAL STIMULATION AT LOW LIGHT LEVELS," *Proceedings of the National Academy of Science*, Early On-line Edition, April 2011) describe exemplary techniques for opto-genetic modification of both cardiac and neural tissue, and are incorporated herein by reference in their entireties. In addition, exemplary techniques for opto-genetic modification of cardiac tissue are described in Bruegmann et al. ("OPTOGENETIC CONTROL OF HEART MUSCLE IN VITRO AND IN VIVO," *Nature Methods*, Vol. 7, No. 11, pp. 897-900, November 2010), which is incorporated herein by reference in its entirety.

Figure 5B:
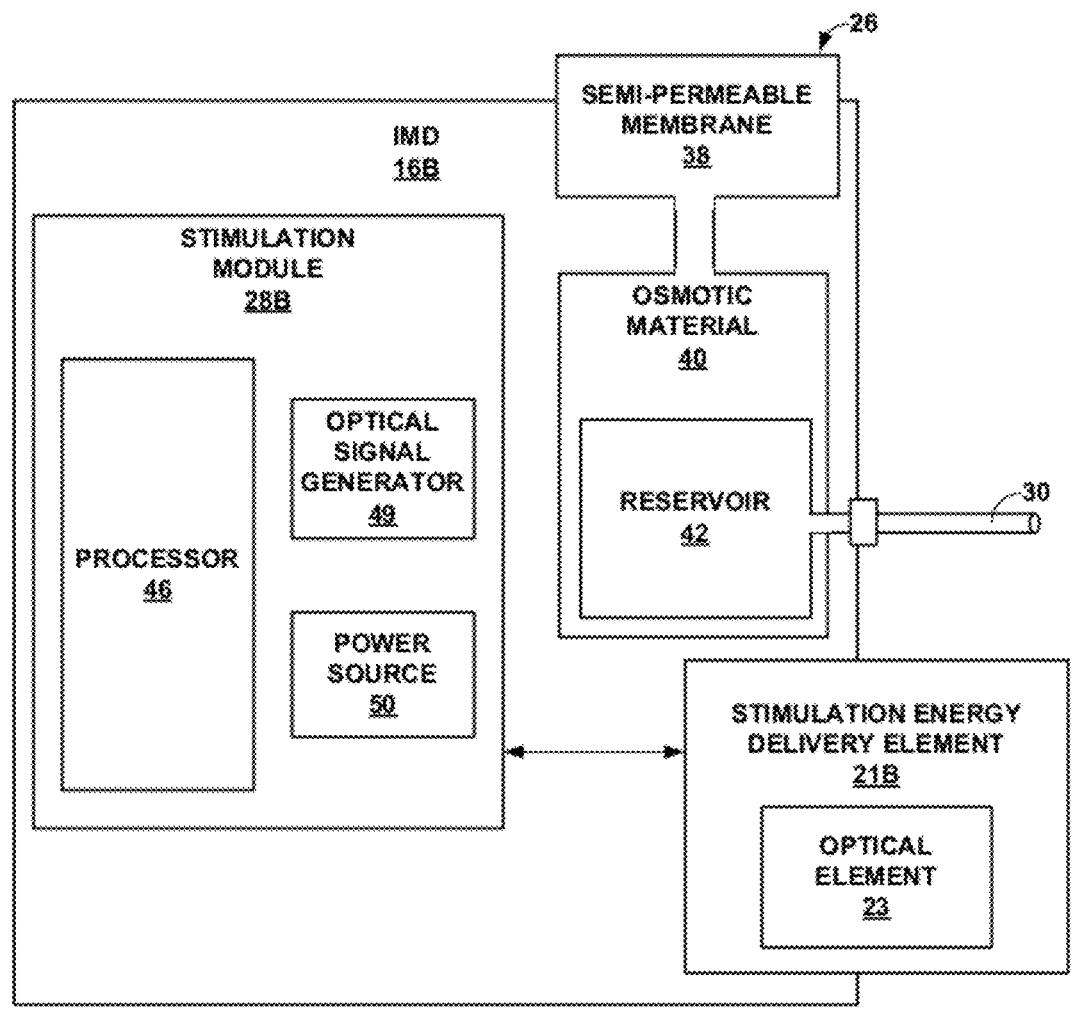
FIG. 5B is a functional block diagram illustrating an example configuration of a leadless IMD that includes an osmotic pump and an optical stimulation delivery element.

As illustrated in FIG. 4B, IMD 16B includes osmotic pump 26 and stimulation module 28B coupled to optical stimulation energy delivery element 23 via optical fiber 45. As described above with respect to FIG. 4A, osmotic pump 26 is configured to store and deliver genetic material to the target tissue site of patient 14. Stimulation module 28B may include any components necessary for delivering optical stimulation to the target tissue site. For example, as illustrated in FIG. 5B, stimulation module 28B may include a processor configured to control the delivery of optical stimulation via optical stimulation energy delivery element 23 and a power source to provide operating power to IMD 16B. In some examples, IMD 16B may also include one or more electrical stimulation electrodes and/or one or more sensing electrodes.

In the example illustrated in FIG. 4B, stimulation module 28B includes any circuitry or other components required for generating and delivering an optical signal, e.g., a light signal, through optical fiber 45 to element 23. Several exemplary systems and techniques for delivering optical stimulation to target tissue of a patient are described in U.S. patent application Ser. No. 12/951,766 by Cong et al., entitled "OPTICAL STIMULATION THERAPY," which was filed on Nov. 22, 2010. U.S. patent application Ser. No. 12/951,766 by Cong et al. is incorporated herein by reference in its entirety.

In some examples, element 23 may be a portion of housing 24 formed from an at least partially transparent or translucent material such that the optical signal transmitted through optical fiber 45 may be projected outward onto the target tissue site, e.g., as illustrated by lines 39, and the optical stimulation energy may be delivered to the target tissue site. For example, element 23 may be formed from an at least partially transparent, biocompatible plastic material. In other examples, optical stimulation energy delivery element 23 may be a different component suitable for delivering optical stimulation energy to the target tissue site. For example, element 23 may itself comprise a light source, e.g., a light emitting diode (LED), such that element 23 may deliver optical stimulation to the target tissue site. In examples in which element 23 itself comprises a light source, element 23 may be coupled to stimulation module 28B via, e.g., a conductor (such as conductor 44) that may transmit an electrical signal to element 23 to provide power to the light source, instead of or in addition to being coupled to stimulation module 28B via optical fiber 45.

In the example illustrated in FIG. 4B, optical fiber 45 extends through osmotic material 40 of osmotic pump 26 to be coupled to element 23. In some examples, the portion of optical fiber 45 within the osmotic material may include an insulated material surrounding the optical fiber such that the osmotic material and the optical fiber do not contact one another. Although FIG. 4B illustrates optical fiber 45 extending through the portion of IMD 16 surrounded by semi-permeable membrane 38 of osmotic pump 26, in other examples, optical fiber 45 may extend through a portion of IMD 16B enclosed by a hermetically-sealed section of housing 24.

FIG. 5A illustrates a functional block diagram of IMD 16A (FIG. 4A), which includes stimulation module 28A, osmotic pump 26, and stimulation energy delivery element 21A that includes housing electrodes 22. As illustrated in FIG. 5, stimulation module 28A may include processor 46, signal generator 47, sensing module 48, and power source 50, and osmotic pump 26 may include semi-permeable membrane 38, osmotic material 40, and reservoir 42.

As discussed previously, semi-permeable membrane 38, osmotic material 40, and reservoir 42 of osmotic pump 26 function cooperatively to deliver genetic material from reservoir 42 via outlet 30 to the target tissue site upon implantation in patient 14, using osmosis. Although FIGS. 4 and 5 illustrate osmotic pump 26 including semi-permeable membrane 38, osmotic material 40, and reservoir 42 to deliver genetic material, in other examples, osmotic pump 26 may include any additional or alternative components necessary or desired for delivering the genetic material to the target tissue site using osmosis. For example, osmotic pump 26 may additionally include, in some examples, a refill port coupled to reservoir 42 such that reservoir 42 may be refilled with genetic material after substantially all of the genetic material stored within reservoir 42 is delivered to the target tissue site. In some examples, a clinician or other user may inject the genetic material into the refill port using a syringe, or other suitable means.

Stimulation module 28A is configured to deliver electrical stimulation to the target tissue site within patient 14 via housing electrodes 22. For example, housing electrodes 22 and stimulation module 28A may form a cardiac stimulator to provide pacing pulses in order to treat a cardiac arrhythmia of patient 12 (e.g., bradycardia, tachycardia, or flutter of patient 12). Housing electrodes 22 may also be sense electrodes that can sense one or more electrical signals indicative of physiological activity at the target tissue site.

Processor 46 of stimulation module 28A is configured to respond to sensing of physiological activity and to control delivery of electrical stimulation via housing electrodes 22. Processor 46 may include any one or more of a microprocessor, a controller, a digital signal processor (DSP), an application specific integrated circuit (ASIC), a field-programmable gate array (FPGA), or equivalent discrete or integrated logic circuitry. In some examples, processor 46 may include multiple components, such as any combination of one or more microprocessors, one or more controllers, one or more DSPs, one or more ASICs, or one or more FPGAs, as well as other discrete or integrated logic circuitry. The functions attributed to processor 46 in this disclosure may be embodied as software, firmware, hardware, or any combination thereof.

Although the examples described herein refer to one or more processors, e.g., processor 46, a processor may be one example of a control module. Thus, in the examples described herein, the term "control module" may include anything referred to herein as a "processor." In some examples, a control module may be configured to perform one or more random logic functions, in addition to other techniques, e.g., instruction-based techniques, described herein.

Signal generator 47 is electrically coupled to stimulation energy delivery element 21A, which includes housing electrodes 22, e.g., via conductors 44 (FIG. 4). Signal generator 47 is configured to generate and deliver electrical stimulation therapy to heart 12. For example, signal generator 47 may deliver pacing pulses to heart 12 via at least two housing electrodes 22. In some examples, signal generator 47 delivers pacing stimulation in the form of electrical pulses. In other examples, signal generator 47 may deliver one or more types of stimulation in the form of other signals, such as sine waves, square waves, or other substantially continuous time signals.

In the examples described herein, a stimulation energy delivery element may include any component positioned on the outer surface of housing 24 or within housing 24 through which stimulation energy is delivered. For example, in the electrical stimulation therapy examples described herein, the stimulation energy delivery element may be one or more electrodes, e.g., housing electrodes 22, positioned on the outer surface of housing 24 through which electrical stimulation is delivered to the target tissue site. As another example, in examples in which optical stimulation therapy is used to treat the disorder of patient 14, the stimulation energy delivery element may be a component through which optical stimulation is delivered to the target tissue site, e.g., a transparent portion of housing 24 or a light source.

Although the examples herein are primarily described with respect to stimulation energy delivery elements positioned on the outer surface of housing 24, in some examples, the stimulation energy delivery elements (e.g., electrodes 22 or an optical stimulation energy delivery element) may be positioned within housing 24. For example, one or more electrodes 22 may be positioned within housing 24 proximate to an opening or aperture defined within housing 24. In this way, the electrodes 22 may be positioned proximate to the target stimulation site such that body fluids at the target stimulation site may conduct the electrical signal transmitted through electrodes 22 to the cells at the target stimulation site.

In examples in which IMD 16 includes more than two housing electrodes 22, signal generator 47 may include a switch module and processor 46 may use the switch module to select, e.g., via a data/address bus, which of the available electrodes 22 are used to deliver stimulation output. The switch module may include a switch array, switch matrix, multiplexer, or any other type of switching device suitable to selectively couple the therapy signal to selected electrodes.

Sensing module 48 monitors signals from at least two or more electrodes 22 in order to monitor electrical activity of heart 12. Sensing module 48 may also include a switch module to select which of the available electrodes 22 are used to sense the heart activity. In some examples, processor 46 may select the electrodes that function as sense electrodes, or the sensing electrode configuration, via the switch module within sensing module 48, e.g., by providing signals via a data/address bus.

Sensing module 48 may include one or more detection channels, each of which may comprise an amplifier. The detection channels may receive cardiac signals. Some detection channels may be configured to detect particular cardiac events within the signals, such as R-waves or P-waves, and provide indications of the occurrences of such events to processor 46. One or more other detection channels may provide the signals to an analog-to-digital converter, for processing or analysis of the signals by processor 46. In response to the control signals from processor 46, the switch module of sensing module 48 may couple selected electrodes to each of the detection channels. Detection of an R-wave by a sensing channel of sensing module 48 may be an example of detection of a cardiac beat.

Processor 46 may include a timing and control module, which may be embodied as hardware, firmware, software, or any combination thereof. The timing and control module may comprise a dedicated hardware circuit, such as an ASIC, separate from other components of processor 46, or a software module executed by a component of processor 46. If IMD 16 is configured to generate and deliver pacing pulses to heart 12, the timing and control module may include programmable counters which control the basic time intervals associated with VVI, AAI, VVIR, AAIR, and other modes of single chamber pacing. In the aforementioned pacing modes, "V" may indicate a ventricle, "I" may indicate inhibited pacing (e.g., pacing able to be inhibited by intrinsic cardiac activity), and "A" may indicate an atrium. The first letter in the pacing mode may indicate the chamber that is paced, the second letter may indicate the chamber that is sensed, and the third letter may indicate the response to sensing.

Intervals defined by the timing and control module within processor 46 may include atrial and ventricular pacing escape intervals, refractory periods during which sensed P-waves and R-waves are ineffective to restart timing of the escape intervals, and the pulse widths of the pacing pulses. As another example, the timing and control module may define a blanking period, and provide signals to sensing module 48 to blank one or more channels, e.g., amplifiers, for a period during and after delivery of electrical stimulation to heart 12. The durations of these intervals may be determined by processor 46 in response to data stored in a memory of IMD 16. The timing and control module of processor 46 may also determine the amplitude of the cardiac pacing pulses.

During pacing, escape interval counters within the timing and control module of processor 46 may be reset upon sensing of R-waves or P-waves with detection channels of sensing module 48. Signal generator 47 may include pacer output circuits that are coupled, e.g., selectively by a switching module, to any combination of electrodes 22 appropriate for delivery of a pacing pulse to one of the chambers of heart 12. Processor 46 may reset the escape interval counters upon the generation of pacing pulses by signal generator 47, and thereby control the basic timing of cardiac pacing functions, including anti-tachyarrhythmia pacing.

In examples in which osmotic pump 26 delivers genetic material to the target tissue site to generate new biological pacemaker cells at the target tissue site, sensing module 48 may sense electrical signals via housing electrodes 22 that indicate that new biological pacemaker cells have been generated at the target tissue site as a result of delivery of the genetic material. For example, sensing module 48 may sense an intrinsic depolarization of heart 12 that was previously not present, which may indicate that the newly generated biological pacemaker cells have sufficiently developed to be capable of intrinsically controlling the rhythm of heart 12. In some examples, upon delivery of genetic material to the target tissue site, processor 46 may incrementally lengthen the escape interval following a sensed event in order to preferentially allow the newly generated biological pacemaker cells to take over pacing of heart 12. If sensing module 48 does not sense an intrinsic depolarization within the lengthened time interval, processor 46 may return the escape interval to an original programmed value. This process allows for hysteresis of the pacing rate in order to preferentially allow intrinsic activity to control the cardiac rhythm and minimize the need for delivery of stimulation energy.

In some examples, upon detecting biological pacemaker activity at the target tissue site, processor 46 may modify the electrical stimulation delivered to the target tissue site. For example, if processor 46 detects an intrinsic depolarization prior to expiration of an escape interval, processor 46 may control signal generator 47 to withhold delivery of the pacing pulse. Processor 46 may also, in response to the intrinsic depolarization, lengthen the escape interval, within limits based on the physiological needs of the patient, to allow the biological pacemaker activity at the target tissue site to take over the pacing of the heart. Over time, processor 46 may thereby entirely suspend delivery of pacing pulses if the newly generated biological pacemaker cells can autonomously maintain a normal rhythm of heart 12.

In examples in which osmotic pump 26 delivers genetic material to the target tissue site to modify properties of the tissue at the target tissue site, sensing module 48 may sense electrical signals via housing electrodes 22 that indicate that properties of the tissue have been modified. In some examples, as discussed previously, the genetic material may be selected to reduce a stimulation threshold required to activate tissue at the target tissue site and, consequently, processor 46 may determine whether the electrical signal sensed by sensing module 48 exhibits characteristics indicative of a reduced stimulation threshold at the target tissue site.

For example, processor 46 may periodically implement a capture detection algorithm and, over time, the results of the capture detection algorithm may indicate a reduced stimulation threshold requirement for heart 12. In order to implement the capture detection algorithm, in some examples, processor 46 may periodically control delivery of electrical stimulation defined by various sets of parameters, e.g., various amplitudes and/or pulse widths, to the target tissue site to identify the capture threshold of heart 12, e.g., a threshold value defining electrical stimulation that results in contraction of heart 12. Over time, after genetic material has been delivered to the target tissue site, the capture detection algorithm may indicate that the capture threshold of heart 12 has been reduced, facilitating delivery of less intense electrical stimulation to the target tissue site to treat the cardiac disorder of the patient and increasing the efficiency of delivery of electrical stimulation via IMD 16.

Upon detecting modified properties of the tissue at the target tissue site, processor 46 may adjust the intensity of the electrical stimulation delivered to the target tissue site. For example, if processor 46 determines that heart 12 requires less intense electrical stimulation for activation of the tissue, e.g., using the capture detection algorithm, processor 46 may control signal generator 47 to reduce an amplitude or pulse width defining the electrical stimulation delivered to the target tissue site. Similarly, if processor 46 determines that heart 12 requires more intense electrical stimulation for activation of the tissue, processor 46 may control signal generator 47 to increase an amplitude or pulse width defining the electrical stimulation delivered to the target tissue site.

The various components of IMD 16 are coupled to power source 50, which may include a rechargeable or non-rechargeable battery. A non-rechargeable battery may be capable of holding a charge for several years, while a rechargeable battery may be inductively charged from an external device, e.g., on a weekly or monthly basis.

In the examples described herein, IMD 16 may require a substantially smaller power source 50 than in examples in which genetic material is not delivered to the target tissue site. For example, as discussed above, delivery of genetic material to the target tissue site may result in, e.g., generation of new biological pacemaker tissue and/or reduction of stimulation threshold requirements at the target tissue site. Consequently, stimulation module 28 of IMD 16 may require less energy for generation of electrical stimulation to treat the cardiac disorder of patient 14, resulting in increased efficiency of IMD 16, particularly after full expression of the genes transferred by the genetic material to the target tissue site.

FIG. 5B illustrates a functional block diagram of IMD 16B (FIG. 4B), which includes stimulation module 28B, osmotic pump 26, and stimulation energy delivery element 21B that includes optical stimulation energy delivery element 23. IMD 16B is configured to delivery optical stimulation therapy to patient 14. As illustrated in FIG. 5B, stimulation module 28B includes optical signal generator 49 configured to generate an optical stimulation signal for delivery to the target tissue site of patient 14 via element 23. IMD 16B may function substantially similarly to IMD 16A (FIG. 5A) except that IMD 16B is configured to deliver optical stimulation therapy to patient 14.

Stimulation module 28B includes any components necessary for generating an optical signal and transmitting the optical signal to element 23 for delivery to the target tissue site. For example, in the example illustrated in FIG. 5B, stimulation module 28B includes processor 46 configured to control delivery of optical stimulation, optical signal generator 49 to generate an optical signal for delivery, and power source 50 to provide power to IMD 16B to carry out the functions of IMD 16B. In some examples, stimulation module 28B may include a passive optical signal generation system such as the system described in U.S. Pat. No. 6,711,440 to Deal et al., entitled "MRI-COMPATIBLE MEDICAL DEVICE WITH PASSIVE GENERATION OF OPTICAL SENSING SIGNALS," which issued on Mar. 23, 2004 and is incorporated herein by reference in its entirety.

As discussed previously with respect to FIG. 4B, optical stimulation energy delivery element 23 may include any component necessary for transmitting optical stimulation to the target tissue site proximate to which element 23 is implanted. For example, as discussed above, element 23 may be a portion of housing 24 formed from an at least partially transparent or translucent material such that the optical signal transmitted through optical fiber 45 may be projected outward onto the target tissue site. In other examples, element 23 may itself comprise a light source which may be powered in any suitable manner, such as by power source 50.

Figure 6:
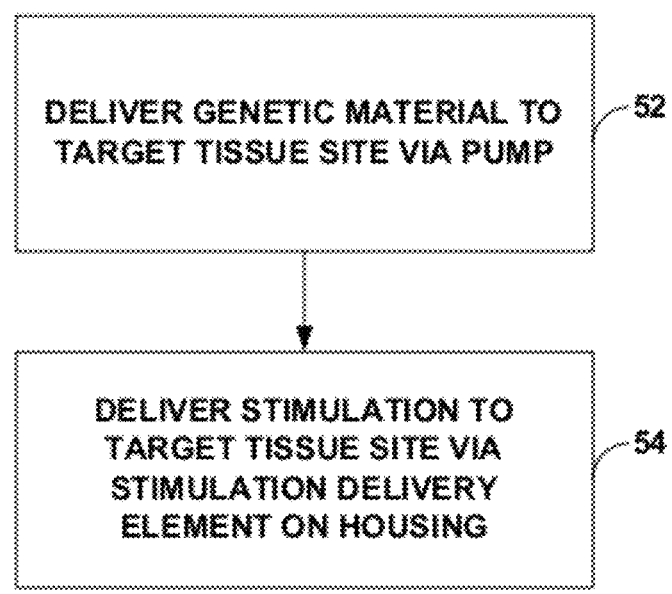
FIG. 6 is a flow diagram illustrating an example technique for delivering genetic material and delivering stimulation to a target tissue site of a patient.

FIG. 6 is a flow diagram illustrating an example technique for delivering genetic material and delivering stimulation to a target tissue site of patient 14 via leadless IMD 16. In the technique illustrated in FIG. 6, osmotic pump 26 of leadless IMD 16 delivers genetic material to the target tissue site within patient 14 (52). As discussed previously, osmotic pump 26 includes a semi-permeable membrane 38, osmotic material 40, and reservoir 42 to deliver the genetic material to the target tissue site via osmosis at a particular rate based on the permeability of semi-permeable membrane 38. Upon delivery of genetic material to the target tissue site, stimulation module 28 controls a signal generator, e.g., electrical signal generator 47 or optical signal generator 49, of leadless IMD 16 to deliver stimulation to the target tissue site via a stimulation energy delivery element 21 (54).

As discussed previously, in some examples, the results of delivery of genetic material to the target tissue site may not immediately take effect, or may not be permanent after they have taken effect. That is, adequate transgene expression within the target tissue site may not be achieved until some time after osmotic pump 26 has delivered the genetic material to the target tissue site, or the results of the transgene expression may not be permanent. Consequently, in some examples, in order to continually treat the disorder of patient 14, stimulation may be delivered to the target tissue site during time periods in which adequate transgene expression at the target tissue site is not evident.

Figure 7:
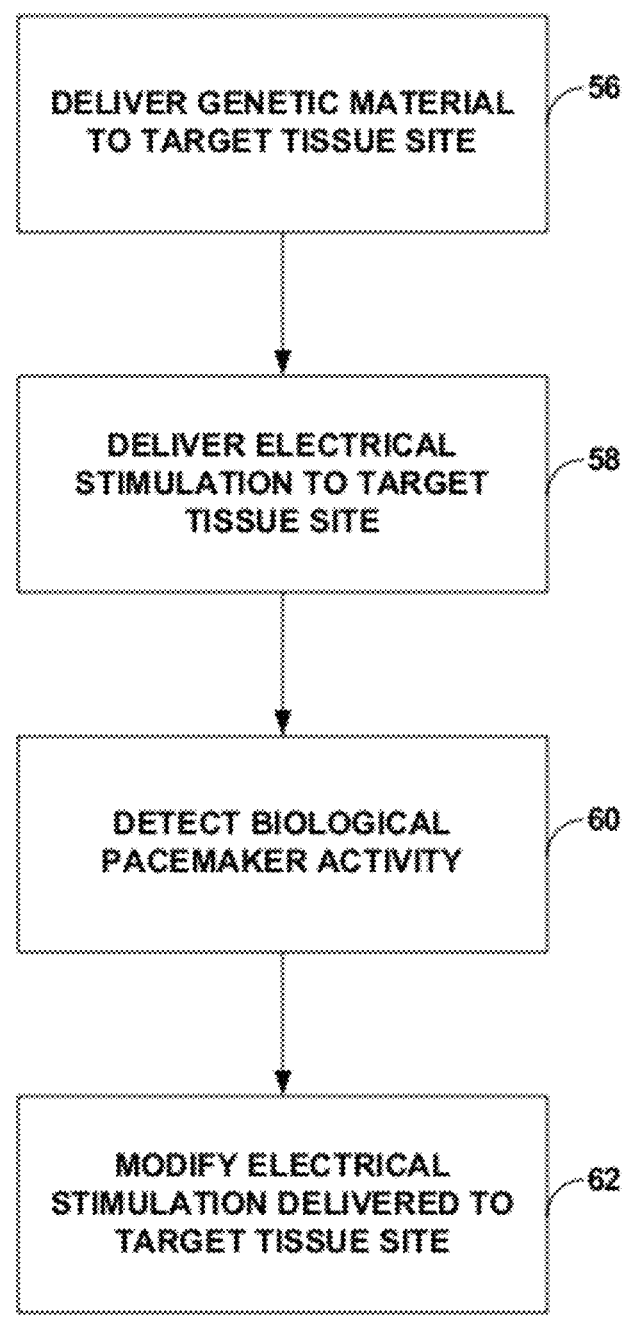
FIG. 7 is a flow diagram illustrating an example technique for modifying electrical stimulation delivered to a target tissue site based on detecting biological pacemaker activity.

FIG. 7 is a flow diagram illustrating an example technique that may be performed by leadless IMD 16 for modifying electrical stimulation delivered to the target tissue site based on detecting biological pacemaker activity at the target tissue site. In the example technique illustrated in FIG. 7, the genetic material delivered to the target tissue site via osmotic pump 26 includes genetic material selected to induce transgene expression to generate new biological pacemaker cells at the target tissue site. As discussed previously, the newly generated biological pacemaker cells may improve the capability of heart 12 to maintain a normal cardiac rhythm autonomously, e.g., without the delivery of electrical stimulation.

According to the technique of FIG. 7, osmotic pump 26 delivers genetic material to the target tissue site (56). Stimulation module 28 simultaneously or subsequently delivers electrical stimulation to the target tissue site (58) to treat the cardiac disorder of patient 14. For example, stimulation module 28 may deliver pacing pulses to heart 12 of patient 14. Processor 46 of IMD 16 subsequently detects biological pacemaker activity, resulting from the newly generate biological pacemaker cells at the target tissue site (60) in any suitable manner. For example, as discussed above, sensing module 48 may sense an intrinsic depolarization of heart 12 that was previously not present, which may indicate that the newly generated biological pacemaker cells have sufficiently developed to be capable of intrinsically controlling the rhythm of heart 12. Over time, the newly generated pacemaker cells may be capable of substantially entirely controlling the rhythm of heart 12.

Because the newly generated biological pacemaker cells may modify the capability of heart 12 to intrinsically maintain a normal cardiac rhythm, based upon detection of biological pacemaker activity at the target tissue site, processor 46 modifies the electrical stimulation delivered to the target tissue site (62). For example, as discussed previously, if processor 46 detects an intrinsic depolarization between a particular sensed depolarization and a particular pacing pulse, e.g., indicative of new biological pacemaker activity, processor 46 may modify delivery of electrical stimulation by withholding one or more subsequent pacing pulses, e.g., by increasing an escape interval for pacing. Over time, processor 46 may thereby entirely suspend delivery of pacing pulses if the newly generated biological pacemaker cells can autonomously maintain a normal rhythm of heart 12.

Figure 8:
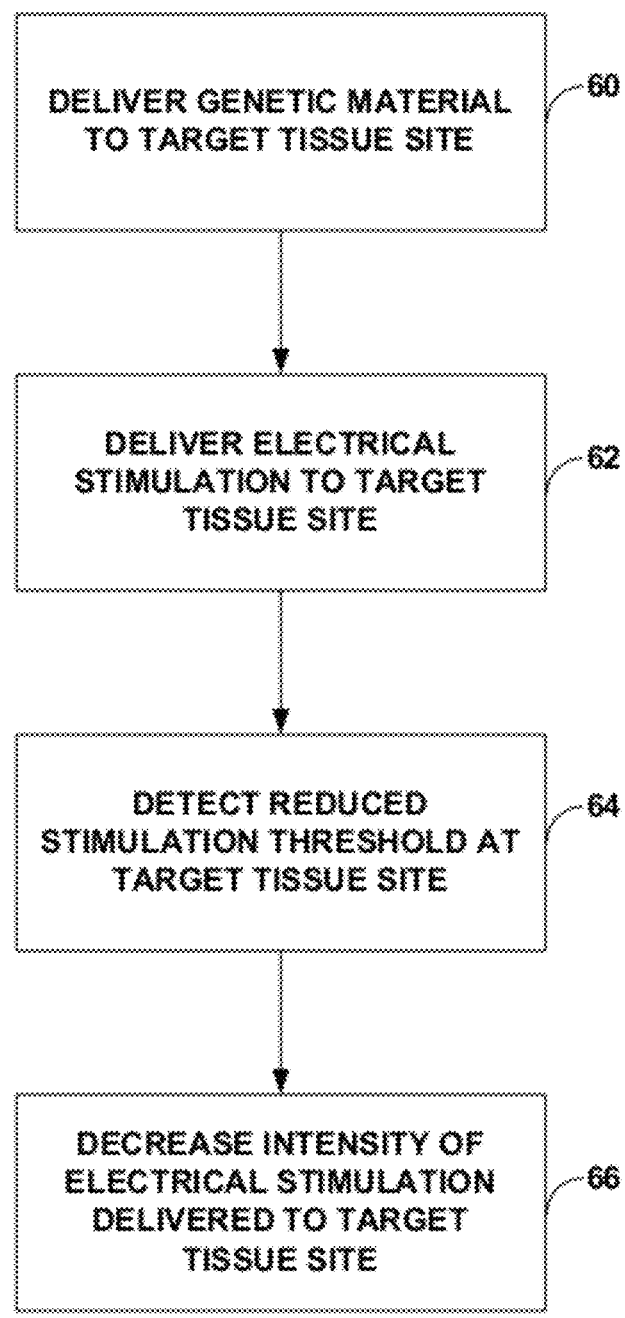
FIG. 8 is a flow diagram illustrating an example technique for decreasing the intensity of electrical stimulation at a target tissue site based on detecting a reduced stimulation threshold at the target tissue site.

FIG. 8 is a flow diagram illustrating an example technique that may be performed by leadless IMD 16 for modifying the intensity of electrical stimulation based on detecting a reduced stimulation threshold at the target tissue site. In the example technique illustrated in FIG. 8, the genetic material delivered to the target tissue site via osmotic pump 26 includes genetic material selected to induce transgene expression to modify properties of existing cells at the target tissue site and, more specifically, to reduce the electrical stimulation threshold required to activate the tissue at the target tissue site. As discussed previously, a reduced stimulation threshold at the target tissue site can increase the efficiency of IMD 16 because less intense stimulation may be required to maintain normal cardiac activity in heart 12.

According to the technique illustrated in FIG. 8, osmotic pump 26 delivers genetic material to the target tissue site (60) using any suitable technique and, simultaneously or subsequently, stimulation module 28 delivers electrical stimulation to the target tissue site via housing electrodes 22 (62) using any suitable technique. Upon delivery of genetic material and electrical stimulation to the target tissue site, processor 46 detects a reduced stimulation threshold in tissue at the target tissue site (64). That is, processor 46 determines that the stimulation threshold requirement for activation of tissue at the target tissue site has been reduced. For example, as discussed previously, processor 46 may periodically implement a capture detection algorithm and, over time, the results of the capture detection algorithm may indicate a reduced stimulation threshold requirement for activation of heart 12. Upon detecting the reduced stimulation threshold requirement, processor 46 may control signal generator 47 to decrease the intensity of electrical stimulation delivered to the target tissue site (66), e.g., by reducing an amplitude or pulse width defining the electrical stimulation.

Figure 9:
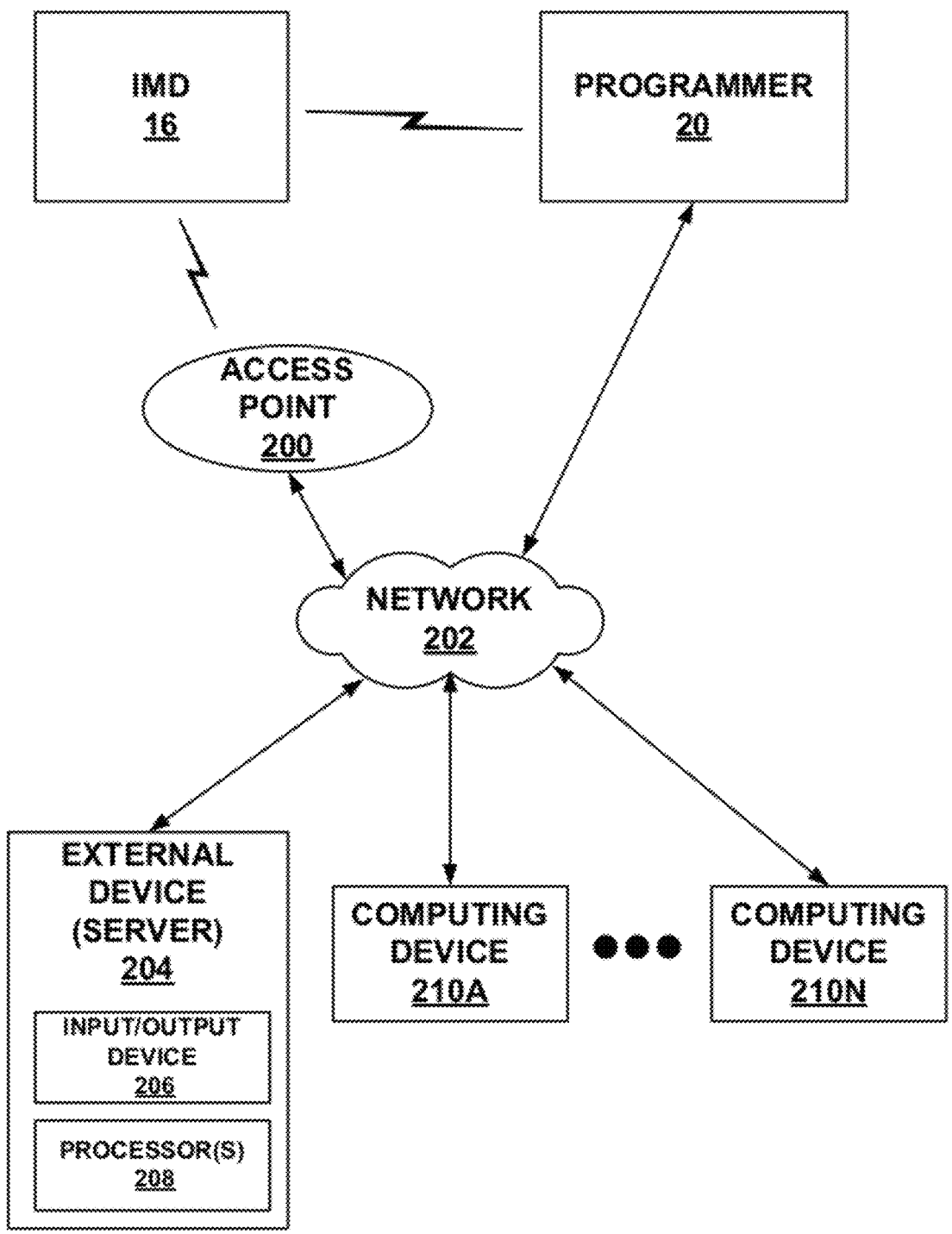
FIG. 9 is a block diagram illustrating an example system that includes an external device, such as a server, and one or more computing devices that are coupled to the IMD and programmer shown in FIG. 1 via a network.

FIG. 9 is a block diagram illustrating an example system 190 that includes an external device, such as a server 204, and one or more computing devices 210A-210N, that are coupled to the IMD 16 and programmer 20 shown in FIG. 1 via a network 202. In this example, IMD 16 may use a telemetry module to communicate with programmer 20 via a first wireless connection, and to communicate with an access point 200 via a second wireless connection. In the example of FIG. 9, access point 200, programmer 20, server 204, and computing devices 210A-210N are interconnected, and able to communicate with each other, through network 202. In some cases, one or more of access point 200, programmer 20, server 204, and computing devices 210A-210N may be coupled to network 202 through one or more wireless connections. IMD 16, programmer 20, server 204, and computing devices 210A-210N may each comprise one or more processors, such as one or more microprocessors, DSPs, ASICs, FPGAs, programmable logic circuitry, or the like, that may perform various functions and operations, such as those described herein. For example, as illustrated in FIG. 9, server 204 may comprise one or more processors 208 and an input/output device 206, which need not be co-located.

Server 204 may, for example, practice the methods described herein. Server 204 may implement any or all of the modules illustrated in FIG. 5 and perform any or all of the techniques illustrated in FIGS. 6-8. Furthermore, in some examples, server 204 may provide a database for storing signal data, which may be provided by server 204 as one example, or by programmer 20 as another.

Access point 200 may comprise a device that connects to network 202 via any of a variety of connections, such as telephone dial-up, digital subscriber line (DSL), or cable modem connections. In other embodiments, access point 200 may be coupled to network 202 through different forms of connections, including wired or wireless connections. In some embodiments, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some embodiments, server 204 or one or more of the computing devices 210A-210N may perform any of the various functions or operations described herein.

Network 202 may comprise a local area network, wide area network, or global network, such as the Internet. In some cases, programmer 20 or server 204 may assemble data related to delivery of genetic material and delivery of electrical stimulation to a target tissue site, in web pages or other documents for viewing by patients and/or trained professionals, such as clinicians, via viewing terminals associated with computing devices 210A-210N. System 190 may thereby permit programming of IMD 16 to allow its operation to be more efficient. For example, system 190 may permit automatic or manual initiation of pacing threshold tests or evaluation of intrinsic cardiac activity. In response, system 190 may reduce the IMD 16 power consumption by manually or automatically adjust the stimulation parameters to be more efficient. System 190 may be implemented, in some aspects, with general network technology and functionality similar to that provided by the Medtronic CareLink® Network developed by Medtronic, Inc., of Minneapolis, Minn.

Although the disclosure is described with respect to cardiac stimulation therapy, such techniques may be applicable to other therapies in which electrical stimulation is delivered to a target tissue site of a patient, such as, e.g., spinal cord stimulation, deep brain stimulation, pelvic floor stimulation, gastric stimulation, occipital stimulation, functional electrical stimulation, and the like. In such therapies, the techniques described in this disclosure may be applied to improve efficiency and efficacy of the electrical stimulation.

The techniques described in this disclosure, including those attributed to IMD 16, programmer 20, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A leadless implantable medical device (IMD) comprising:
   a housing defining an outer surface and comprising an outlet;
   a pump reservoir positioned within the housing, wherein the pump reservoir is configured to store genetic material, wherein the genetic material is configured to generate at least one of a reduced stimulation threshold or new intrinsic biological pacemaker activity at a target cardiac tissue site of a patient adjacent to the outer surface of the housing, and wherein the genetic material is configured to generate the at least one of the reduced stimulation threshold or the new intrinsic biological pacemaker activity by at least inducing transgene expression to generate biological pacemaker cells in the cardiac tissue of the patient, wherein the biological pacemaker cells are capable of inducing a normal cardiac rhythm autonomously;
   a pump positioned within the housing, wherein the pump is configured to deliver the genetic material to the target cardiac tissue site via the outlet;
   a stimulation energy delivery element positioned on or within the housing; and
   a stimulation module within the housing and coupled to the stimulation energy delivery element, wherein the stimulation module is configured to deliver cardiac pacing to the target cardiac tissue site via the stimulation energy delivery element, the stimulation module comprising a control module configured to detect the at least one of the reduced stimulation threshold or the new intrinsic biological pacemaker activity in response to the delivery of the genetic material to the target cardiac tissue site via the pump and modify at least one parameter defining the stimulation in response to the detection of the at least one of the reduced stimulation threshold or the new intrinsic biological pacemaker activity at the target cardiac tissue site.

2. The leadless IMD of claim 1, wherein the stimulation module comprises an electrical signal generator configured to generate an electrical signal, and wherein the stimulation energy delivery element comprises a plurality of housing electrodes, wherein the electrical signal generator of the stimulation module is configured to deliver electrical stimulation to the target cardiac tissue site via the plurality of housing electrodes.

3. The leadless IMD of claim 1, wherein the stimulation module comprises an optical signal generator configured to generate an optical signal, and wherein the stimulation energy delivery element comprises an optical energy delivery element, wherein the optical signal generator of the stimulation module is configured to deliver optical stimulation to the target cardiac tissue site via the optical energy delivery element.

4. The leadless IMD of claim 3, wherein the optical energy delivery element comprises a portion of the housing formed from an at least partially transparent material.

5. The leadless IMD of claim 1, wherein the stimulation module comprises an electrical signal generator configured to generate an electrical signal, and wherein the stimulation energy delivery element comprises a light source, wherein the electrical signal generator is configured to deliver energy to the light source such that the light source delivers optical stimulation to the target stimulation site.

6. The leadless IMD of claim 1, wherein the genetic material is configured to generate at least one of a reduced stimulation threshold or new intrinsic biological pacemaker activity by at least inducing transgene expression to reduce a stimulation threshold of cells in the cardiac tissue of the patient.

7. The leadless IMD of claim 1, wherein the genetic material comprises genetic material delivered within a capsid of an adeno-associated virus.

8. The leadless IMD of claim 1, further comprising a fixation element coupled to the outer surface of the housing, wherein the fixation element is configured to secure the leadless IMD within the patient proximate to the target cardiac tissue site of the patient.

9. The leadless IMD of claim 8, wherein the fixation element comprises a tine extending outward from the outer surface of the housing.

10. The leadless IMD of claim 1, wherein the control module is configured to detect the at least one of the reduced stimulation threshold or the new intrinsic biological pacemaker activity by at least determining a capture threshold of tissue at the target cardiac tissue site, and wherein the control module is configured to modify the at least one parameter defining the stimulation by at least modifying the at least one stimulation parameter defining the stimulation based on determining the capture threshold.

11. The leadless IMD of claim 1, wherein the control module is configured to detect the at least one of the reduced stimulation threshold or the new intrinsic biological pacemaker activity by at least implementing a capture detection algorithm to detect the reduced stimulation threshold at the target cardiac tissue site, and wherein the control module is configured to modify the at least one parameter defining the stimulation by at least modifying the at least one parameter defining the stimulation based on detecting the reduced stimulation threshold at the target cardiac tissue site.

12. The leadless IMD of claim 1, wherein the control module is configured to detect the at least one of the reduced stimulation threshold or the new intrinsic biological pacemaker activity by at least detecting the new intrinsic biological pacemaker activity at the target cardiac tissue site, and wherein the control module is configured to modify the at least one parameter defining the stimulation by at least decreasing or suspending delivery of stimulation to the target cardiac tissue site based on detecting the new intrinsic biological pacemaker activity at the target cardiac tissue site.

13. The leadless IMD of claim 1, wherein the pump comprises an osmotic pump.

14. A method comprising:
delivering, via a pump of a leadless implantable medical device, genetic material to a target cardiac tissue site of a patient, wherein the genetic material is configured to generate at least one of a reduced stimulation threshold or new intrinsic biological pacemaker activity at the target cardiac tissue site of the patient, wherein the genetic material is configured to generate the at least one of the reduced stimulation threshold or the new intrinsic biological pacemaker activity by at least inducing transgene expression to generate biological pacemaker cells in the cardiac tissue of the patient, wherein the biological pacemaker cells are capable of inducing a normal cardiac rhythm autonomously, and wherein the leadless implantable medical device comprises:
a housing defining an outer surface and comprising an outlet,
a pump reservoir positioned within the housing, wherein the pump reservoir is configured to store the genetic material,
the pump positioned within the housing,
a stimulation energy delivery element positioned on or within the housing, and
a stimulation module within the housing and coupled to the stimulation energy delivery element, the stimulation module comprising a control module;
delivering, via the stimulation module, stimulation to the target cardiac tissue site of the patient via the stimulation energy delivery element, wherein the target cardiac tissue site is adjacent to the outer surface of the housing;
detecting, via the control module, the at least one of the reduced stimulation threshold or the new intrinsic biological pacemaker activity in response to the delivery of the genetic material to the target cardiac tissue site via the pump; and
modifying, via the control module, at least one parameter defining the stimulation in response to the detection of the at least one of the reduced stimulation threshold or the new intrinsic biological pacemaker activity at the target cardiac tissue site.

15. The method of claim 14, wherein detecting the at least one of the reduced stimulation threshold or the new intrinsic biological pacemaker activity comprises implementing a capture detection algorithm to detect the reduced stimulation threshold at the target cardiac tissue site, and wherein modifying the at least one parameter defining the stimulation comprises modifying the at least one parameter defining the stimulation based on detecting the reduced stimulation threshold at the target cardiac tissue site.

16. The method of claim 14, wherein detecting the at least one of the reduced stimulation threshold or the new intrinsic biological pacemaker activity comprises detecting, with the control module, the new intrinsic biological pacemaker activity at the target cardiac tissue site, and wherein modifying the at least one parameter defining the stimulation comprises decreasing or suspending delivery of stimulation to the target cardiac tissue site based on detecting the new intrinsic biological pacemaker activity at the target cardiac tissue site.

17. The method of claim 14, wherein the pump comprises an osmotic pump.

* * * * *